United States Patent [19]
Stewart

[11] Patent Number: 5,962,445
[45] Date of Patent: Oct. 5, 1999

[54] TREATMENT OF ASTHMA AND AIRWAY DISEASES

[75] Inventor: Alastair George Stewart, Melbourne, Australia

[73] Assignee: Amrad Operations Pty Ltd., Richmond, Australia

[21] Appl. No.: 08/853,528

[22] Filed: May 9, 1997

[30] Foreign Application Priority Data

May 9, 1996 [AU] Australia ................................. PN9766
May 20, 1996 [AU] Australia ................................. PN9918

[51] Int. Cl.$^6$ ..................................................... A61K 31/56
[52] U.S. Cl. ............................................. 514/182; 514/826
[58] Field of Search ...................................... 514/182, 826

[56] References Cited

U.S. PATENT DOCUMENTS

| | | |
|---|---|---|
| 4,420,428 | 12/1983 | Varma . |
| 4,529,547 | 7/1985 | Varma . |
| 4,529,548 | 7/1985 | Varma et al. . |

FOREIGN PATENT DOCUMENTS

| | | |
|---|---|---|
| 0 144 086 | 12/1985 | European Pat. Off. . |
| 0 172 672 | 2/1986 | European Pat. Off. . |
| 0 452 914 A2 | 10/1991 | European Pat. Off. . |
| 08165242 A2 | of 1996 | Japan . |
| WO 92/22287 | 12/1992 | WIPO . |
| WO 92/22288 | 12/1992 | WIPO . |
| WO 94/14834 | 7/1994 | WIPO . |
| WO 95/04535 | 2/1995 | WIPO . |
| WO 95/20393 | 8/1995 | WIPO . |

OTHER PUBLICATIONS

Lee et al., "Anti–Inflammatory Steroids: Research Trends And New Compounds", *Drugs of Today* vol. 25, No. 9, pp. 577–588 (1989).

Richards et al., "Novel Steroid–Based Inhibitors Of Lung Inflammation", *Clinical and Experimental Allergy*, vol. 22, pp. 432–439 (1992).

Nishigaka et al., "Anti–Proliferative Effect Of 2–Methoxyestradiol On Cultured Smooth Muscle Cells From Rabbit Aorta", *Atherosclerosis* 113, pp. 167–170 (1995).

Fotsis et al., "The Endogenous Oestrogen Metabolite 2–Methoxyoestradiol Inhibits Angiogenesis And Suppresses Tumour Growth", *Letters To Nature*, vol. 368, pp. 237–239 (1994).

Nicoletti et al. Brain Research, 279 (1–2) 352–8 (Abstract), 1983.

Scheinmann et al Revue Dupraticien, 42 (19) 2437–46 (France) (Abstract), 1992.

Chandler et al. Pharmacotherapy, 17 (2) 224–34 (Abstract), 1997.

*Primary Examiner*—Kevin E. Weddington
*Attorney, Agent, or Firm*—Merchant & Gould P.C.

[57] ABSTRACT

The invention relates to use of steroids or steroid analogues in the treatment of chronic and acute inflammation of the airways, particularly asthmatic conditions. It also relates to compounds and compositions which modulate airway remodelling. In a preferred embodiment, the steroid is 2-methoxyoestradiol.

9 Claims, 15 Drawing Sheets

TREATMENT OF ASTHMA AND AIRWAY DISEASES

This invention relates to a method of treating chronic and acute inflammation of the airways, including asthmatic conditions. The invention also relates to steroid or steroid analogues used in the treatment, and to pharmaceutical compositions comprising these compounds as the active agent. In a preferred embodiment, the active component inhibits inflammation and smooth muscle cell proliferation in the airway wall. It may also have at least one other activity selected from anti-angiogenesis, anti-oxidation and the ability to disrupt microtubule formation.

BACKGROUND OF THE INVENTION

Two distinct classes of agents are currently used in the treatment of asthma. Symptomatic relief is provided by using bronchodilators which include the $\beta_2$-adrenoceptor agonists such as salbutamol and salmeterol. Other agents with bronchodilatory properties include the muscarinic-receptor antagonist, ipratropium bromide, and phosphodiesterase inhibitors such as theophylline.

The second class of agents is prophylactic, and includes glucocorticoids such as beclomethasone dipropionate. Disodium cromoglycate and nedocromil sodium are also used, even though these are less effective than the glucocorticoids.

However, none of these agents completely reverses airway hyperresponsiveness or prevents catastrophic life-threatening and fatal episodes of asthma in all patients. The fact that these conditions prevail and sometimes are the cause of death highlights the fact that the benefits from these agents are sub-optimal.

Asthma is now regarded as a disease of chronic airways inflammation characterised by eosinophilic bronchitis [Frigas et al., 1991]. In common with other chronic inflammatory diseases, the inflammation in asthma initiates tissue remodelling, which has been documented in the airways in post mortem studies [Dunnill et al., 1969] and by bronchial biopsy from living donors [Brewster et al., 1990; Bai & Pare, 1995]. The remodelling involves: epithelial sloughing; marked infiltration of eosinophils into the mucosa; activation of mast cells and lymphocytes; enlargement of mucous glands; deposition of wound-type collagen immediately below the true basement membrane of the epithelium and throughout the mucosa; and an increase in the number of myofibroblasts. In addition, there is an increase in the volume and number of blood vessels in asthmatic airways, indicating that an angiogenesis accompanies the remodelling process [Kuwano et al., 1993]. The overall volume of the airway wall is increased [James et al., 1989] in association with an increase in the volume of airway smooth muscle [Kuwano et al., 1993] which results from both hypertrophic and hyperplastic responses [Ebina et al., 1993].

Airway hyperresponsiveness (AHR) is the excessive bronchoconstrictor response of asthmatic subjects to a diverse array of stimuli. The concept that the airway wall thickening is central to the development of AHR has gained acceptance during the last 10 years. The thickening of the airways has been shown by mathemathical modelling studies to amplify the consequences of smooth muscle shortening-a given amount of smooth muscle shortening is calculated to cause a much greater increase in airways resistance in asthmatics compared with healthy subjects (eg 40% shortening gives a 15-fold increase in healthy subjects, but a 290-fold increase in asthmatics) [James et al., 1989]. The airway wall area is increased by 50–250%, with larger increments being observed in the larger airways [James et al., 1989]. The muscle increases in volume by 2–3 fold, and the extent of the increase is related to the severity of asthma [Kuwano et al., 1993]. The nature of the change has not been extensively investigated, but it comprises both hyperplagia and hypertrophy [Ebina et al., 1993]. After prolonged allergen avoidance by allergic asthmatics, decreases in airways responsiveness to the levels observed in healthy subjects have been demonstrated, and are accompanied by a resolution of the symptoms [Platts-Mills et al., 1987]. Studies such as this are consistent with the notion that the structural changes in the asthmatic airway are also reversible.

These long-term changes in the asthmatic airway offer new targets for therapeutic intervention [Stewart et al., 1993]. Consequently there has been considerable interest in identifying the mechanisms for this airway wall remodelling response and the influence of existing anti-asthma drugs on these processes. A large number of factors have been established as mitogens for cultured airway smooth muscle from various species, including humans [see Stewart et al., 1995a for a review]. as expected, the stimuli belonging to the growth factor families, including basic fibroblast growth factor (bFGF), platelet-derived growth factor (PDGF$_{BB}$) and epidermal growth factor (EGF) are the most effective proliferative agents [Hirst et al., 1992; Stewart et al., 1995a]. Thrombin is also an effective growth factor [Tomlinson et al., 1994], whereas bronchoconstrictors such as endothelin-1 and the thromboxane $A_4$ mimetic, U46619, are only weakly active, and some other constrictors such as histamine and neurokinins are completely inactive [Stewart et al., 1995a].

In human cultured airway smooth muscle, continuous exposure to $\beta$-adrenoceptor agonists reduces the proliferative responses to a wide range of mitogens, including thrombin, EGF and the thromboxane $A_2$ analogue, U46619 [Tomlinson et al., 1994; 1995]. Furthermore, dexamethasone and other anti-inflammatory steroids also have an anti-proliferative effect on cultured airway smooth muscle [Stewart et al., 1995b], but the magnitude of the inhibition depends on the mitogen that stimulates proliferation in the first instance. It is also important to note that long-term treatment with inhaled anti-inflammatory steroids produces only a modest reduction in AHR [Sotomayor et al., 1984; Lungren et al., 1988], whereas $\beta_2$-agonists are reported to have either no effect or to increase AHR [Wahedna et al., 1993]. Thus, the two most commonly used and most effective drug classes for the treatment of asthma have sub-optimal effects on AHR, and are therefore unlikely to be effective in regulating the structural changes associated with airway remodelling that contribute to the progression and development of the condition.

We have been investigating potential ways of arresting or modulating the remodelling process and have surprisingly identified a steroid and analogues thereof which are suitable for this purpose.

SUMMARY OF THE INVENTION 2-methoxyoestradiol is a natural metabolite of 17$\beta$-oestradiol, the physiological estrogen in humans.

It is produced in a two-step process, involving hydroxylation of estrogen to produce a catecholoestrogen followed by methoxylation to produce the corresponding methoxyoetrogen by an inducible cytochrome p450 pathway [Spink et al., 1994]. Hitherto considered to be biologically inactive [Rosner et al., 1991], in cell culture studies it has been established that 2-methoxyoestradiol inhibits proliferation of certain transformed cell lines [Lottering et al., 1992] and of actively proliferating or non-quiescent endothelical cells and fibroblasts [Fotsis et al., 1994]. Fotsis et al also showed that administration of 2-methoxyoestradiol inhibited the growth of tumours by suppressing tumour-induced angiogenesis, rather than by direct inhibition of tumour cell proliferation. It was proposed that the compound reduced basal membrane breakdown, thus preventing cell migration into the extracellular matrix and rendering it a potential anti-angiogenic agent for the treatment of solid tumors or angiogenic diseases. Inhibition of tumour neovascularization was also demonstrated in Klauber et al, 1997.

The anti-proliferative effects of 2-methoxyoestradiol on cultured smooth muscle cells from rabbit aorta [Nishigaki et al., 1995] also suggested the usefulness of this compound in the prevention of progresion of atherosclerosis, a disease caused by cellular events that differ from those seen in asthma and AHR.

The mechanism of the anti-proliferative effects ha not yet been established. Lottering et al. (1992) suggested that elevation of cyclic adenosine monophosphate (cAMP) explains the inhibitory effects of 2-methoxyoestradiol on DNA synthesis, whereas inhibition of microtubule assembly during spindle formation in mitosis is considered to explain the inhibitory effects on cell division [Fotsis et al., 1994]. The other biological effects of 2-methoxyoestradiol are not extensively characterized. In pig endometrial cell cultures, 2-methoxyoestradiol inhibits the synthesis of $PGF_{2\alpha}$ [Zhang & Davis, 1992]. Non-genomic actions of 2-methoxyoestradiol include microtubule disruption via binding at the colchicine site on tubulin [D'Amato et al., 1994; Aizu-Yokota et al., 1995] and relaxation of vascular smooth muscle [Goyache et al., 1995].

In International patent publication No. WO95/04535, estradiol derivatives which exert anti-mitotic effects by inhibiting tubulin polymerisation in vitro are disclosed. It is inferred from the in vitro studies that the compounds inhibit endothelial cell proliferation.

The present invention relates to effects of 2-methoxyoestradiol and inhibition of inflammatory cell activation. It particularly relates to treatment or prevention of airway diseases such as asthma.

None of the documents referred to above suggest or disclose the invention. For example, inhibition of smooth muscle cell proliferation and inflammatory cell activation in the airway cannot be predicted by the in vitro observations described in WO95/04535 and the mechanism of these activities do not appear to be related to actions on microtubule assembly.

The anti-proliferative effect of 2-methoxyoestradiol on rabbit vascular smooth muscle [Nishigaki et al, supra] also cannot be extrapolated to airway smooth muscle, since there are known differences in responsiveness of the cells from these two different sources.

Some agents which enhance endothelial cell proliferation, eg. heparin, actually inhibit proliferation of airway smooth muscle cells. Therefore, the anti-proliferative effects of 1-methoxyoestradiol in endothelial cells [Fotsis et al, WO95/04535, supra] do not suggest that smooth muscle would respond in the same way.

We have found that 2-methoxyoestradiol inhibits the release of myeloperoxidase from polymorphonuclear leukocytes obtained from human peripheral blood, as well as the phagocytic activity of these cells. The reduction of phagocytic activity in these cells provides evidence of its anti-inflammatory properties. This is surprising, particularly because 2methoxyoestradiol is known not to have significant affinity for glucocorticoid or for estrogen receptors [Merriam et al, 1980].

These properties render 2-methoxyoestradiol and related compounds of benefit in the treatment of conditions which include but are not limited to asthma, chronic obstructive airway diseases and other airway diseases characterised by inflammation. Other conditions amenable to treatment by the methods of the invention include, for example, emphysema, pneumonia or airway diseases characterised by one or both of proliferative and inflammatory conditions eg. neutrophil infiltration, or pulmonary infectious diseases the symptoms or sequelae or which result from activation of resident and inflammatory cells.

Conditions such as allergic rhinitis may also be treated, since we have also found that 2-methoxyoestradiol inhibits degranulation of the mast cell-related cell line, RBL2H3. This inhibitory effect of 2-methoxyoestradiol was selective for antigen-stimulated release since the response to the protein kinase C stimulant, PMA, and to the calcium ionophore A23187, were unaffected. Thus, the effect on antigen release is not likely to result from a non-specific action on microtubule-dependent granule extrusion. Our results indicate that 2-methoxyoestradiol and related steroids having these activities are useful for treating allergic conditions that include but are not limited to rhinitis and atopic skin conditions. Without wishing to be bound to any particular mechanism of action, these data suggest that specific, signal transduction mechanisms involving receptors are involved and contribute to the inhibition of inflammatory in the airway.

We have further found that 2-methoxyoetradiol inhibits DNA synthesis and cell division in airway smooth muscle stimulated with a range of growth factors, including FCS and bFGF. In addition, serotonin-stimulated increases in protein synthesis rates are inhibited by 2-methoxyoestradiol, raising the possibility of anti-hypertrophic effects, in addition to inhibition of cell proliferation. Our observations, together with the anti-angiogenic activity of 2-methoxyoetradiol, indicate that this and related compounds may have therapeutic value in the treatment of airway diseases characterised by inflammation as described above, in particular in the treatment of chronic asthma, with particular impact on the airway wall remodelling and hence on airway hyperresponsiveness. Analogues of 2-methoxyoestradiol were also tested for their ability to inhibit DNA synthesis, and the results indicate that these also may have therapeutic value.

In a first aspect, the invention provides a method of treating a disease characterised by chronic or acute airway inflammation, comprising the step of administering a steroid or steroid analogue having the ability to modulate remodelling of the airway to a mammal in need of such treatment. Preferably the mammal is a human, cat, horse or bovine, and more preferably is human. The steroid 2-methoxyoestradiol is especially preferred for use in accordance with the method of the invention. Steroids or analogues thereof which do not have effective glucocorticoid activity at the dosage level used in accordance with this invention are particularly desired.

In a second aspect, the invention provides a method of treating a disease characterised by chronic or acute airway inflammation, comprising the step of administering a steroid or steroid analogue to a mammal in need of such treatment, wherein said steroid or analogue inhibits phgocytic activity of polymorphonuclear leucocytes. Preferably, the release of myeloperoxidase from the leucocytes is also inhibited. The activation of macrophages may also be inhibited.

In one embodiment, the method according to the invention further modulates remodelling of the airway by inhibiting smooth muscle cell proliferation and inflammation. The remodelling may further be modulated by inhibition of one or more activities selected from the group consisting of angiogenesis, formation of oxidants and microtubule function in the airway wall.

In a particularly preferred embodiment, the method of the invention is used in the treatment of a disease selected from the group consisting of asthma, airway hyperresponsiveness, brochoconstriction, emphysema, pneumonia, atopic disease such as allergic rhinitis and pulmonary infection.

In a third aspect, the invention provides a steroid or steroid analogue which modulates airway remodelling by inhibiting inflammation of the airway wall. Preferably, the compound also has the ability to inhibit proliferation of airway smooth muscle cells, particularly in response to a mitogenic stimulus.

In a fourth aspect, the invention relates to a steroid or steroid analogue which modulates airway remodelling by inhibiting phagocytic activity. In a preferred embodiment, the phagocytic activity of polymorphonuclear leucocytes is inhibited by 2methoxyestradiol. In another embodiment, the release of myeloperoxidase from polymorphonuclear leucocytes is also suppressed. In a particularly preferred embodiment, the steroid or steroid analogue does not exhibit glucocorticoid activity.

In a fifth aspect, the invention provides a steroid or analogue as described above, further having anti-angiogenic activity and/or anti-oxidant activity. In a particularly preferred embodiment, the steroid or steroid analogue of the invention also has the ability to disrupt microtubules in the airway wall.

In a sixth aspect, the invention provides a composition comprising a steroid or steroid analogue as described above, optionally together with one or more pharmaceutically acceptable carriers and excipients. Examples of such carriers and excipients include but are not limited to dry micronised powders together with lactose, or recently developed hydrofluoroalkanes. The composition of the invention may be used in formulations for administration via any standard route used in treatment of airway diseases or asthma, for example, topical, oral, nasal administration or by inhalation. These formulations may be in any conventional form such as capsules, cachets, tablets, aerosols, powder granules, micronised particles or as a solution. Optionally, the steroid or steroid analogue may be complexed with cyclodextrin, and may also be in the form of an ester formed with a pharmaceutically acceptable acid such as sulphate, acetate, benzoate or the like. A person skilled in the art will be able by reference to standard texts, such as Remington's Pharmaceutical Sciences $17^{th}$ edition, to determine how the formulations are to be made and how these may be administered.

The dose of the steroid or steroid analogue to be administered will depend on the condition to be treated and the route of administration, and will be at the discretion of the attending physician or veterinarian. Such a person will readily be able to determine a suitable dose, mode and frequency of adminitration. The composition of the invention may be used to treat conditions of chronic or acute airway inflammation, including asthma, airway hyperresponsiveness (AHR) or bronchoconstriction.

Administration

The compositions described above can be provided as physiologically acceptable formulations using known techniques, and these formulations can be administered by standard routes. In general, the combinations may be administered by the topical, oral, rectal or parenteral (e.g., intravenous, subcutaneous or intramuscular) route. In addition, the combinations may be incorporated into biodegradable polymers allowing for sustained release, the polymers being implanted in the vicinity of where delivery is desired, for example, at the site of a tumor. The biodegradable polymers and their use are described in detail in Brem et al., J. Neurosurg. 74:441–446 (1991).

The dosage of the composition will depend on the condition being treated, the particular derivative used, and other clinical factors such as weight and condition of the patient and the route of administration of the compound. However, for oral administration to humans, a dosage of 0.01 to 100 mg/kg/day, preferably 0.01–1 mg/kg/day, is generally sufficient.

The formulations include those suitable for oral, rectal, nasal, topical (including buccal and sublingual), vaginal or parenteral (including subcutaneous, intramuscular, intravenous, intradermal, intraocular, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tables may be made by molding, in a suitable machine, a mixture of the powdered compound moistened with an inert liquid diluent. The tablets may optionally be coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin be presented as ointments, creams, gels and pastes comprising the ingredient to be administered in a pharmaceutical acceptable carrier. A preferred topical delivery system in a transdermal patch containing the ingredient to be administered.

Formulations for rectal administration may be presented as a suppository with a suitable base comprising, for example, coca butter or a salicylate.

Formulations suitable for nasal administration, wherein the carrier is a solid, include a coarse powder having a particle size, for example, in the range of 20 to 500 microns which is administered in the manner in which snuff is taken, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the additions of the sterile liquid carrier, for example, water for injections, immediately prior to use. Extemporaneous injection solutions and suspensions may be prepared from sterile powders, granules and tables of the kind previously described.

Preferred unit dosage formulations are those containing a daily dose a unit, daily sub-dose, as herein above recited, or an appropriate fraction thereof, of the administering ingredient.

It should be understood that in addition to the ingredients, particularly mentioned above, the formulations of this invention may include other agents convention in the art having regard to the type of the formulation in question, for example, those suitable for oral administration may include flavoring agents.

In a particularly preferred embodiment of the invention, inflammation and proliferation of smooth muscle cells in the airway in the wall of an asthmatic patient is inhibited by administration of a composition comprising 2-methoxyoetradiol.

Although the invention will be described with particular reference to 2-methoxyoestradiol, it will be understood that analogues of this compound which have the requisite biological activities may also be used in accordance with the invention. These include but are not limited to 2-hydroxyestradiol, 2-methoxyoestradiol-3 methyl ether and 4-methoxyoetradiol.

A variety of compounds have been identified as oestradiol derivatives having anti-proliferative and/or anti-angiogenic activity in other tissues. See, for example, WO95/04535 the entire disclosure of which is incorporated herein by this reference.

Such compounds may be suitable candidates for use in accordance with the present invention and are within the meaning of steroids, steroid analogues or steroid-like compounds for the purpose of the present invention. Preferred compounds have a methoxy group at the 2position of the steroid backbone.

In addition, it is contemplated that further compounds not hitherto known will have sufficient structural similarity to the 2-methoxy steroids or steroid-like compounds of this invention to have biological activities within the scope of this invention. For the purposes of this specification, the terms "steroid", "steroid analogue" or "steroid-like" are to be understood to encompass 2-methoxyoestradiol., 2-hydroxyoestradiol, 2-methoxyoestradiol-3, methyl ether, 4-methoxyoestradiol and other compounds based around a steroid nucleus that have the relevant biological activities to be used for the purpose of the present invention. Other compounds may have sufficient structural and/or electronic resemblance (charge distribution) to 2-methoxyoestradiol and have biological activities within the scope of this invention without strictly having a steroid nucleus, such compounds are to be considered steroid analogous for the purposes of the present invention, for example compounds of WO95/04535. Compounds with such activities may be readily identified by using assays capable of indicating activities of the type described elsewhere in this specification. As an example, a compound may be tested for its effects on chronic respiratory obstructive disease by measuring airway smooth muscle cell proliferation; effects on allergic rhinitis and on infectious diseases may be tested by determining the inhibition of inflammatory cell activation, eg. mast cells for rhinitis and neutrophils for infectious disease.

A person skilled in the art will be aware of alternative tests and can readily screen compounds for use in accordance with the invention.

BRIEF DESCRIPTION OF THE DRAWINGS

The invention will now be described in detail by way of example only, with reference to the following figures in which.

DETAILED DESCRIPTION OF THE INVENTION

Abbreviations

Figure 1:
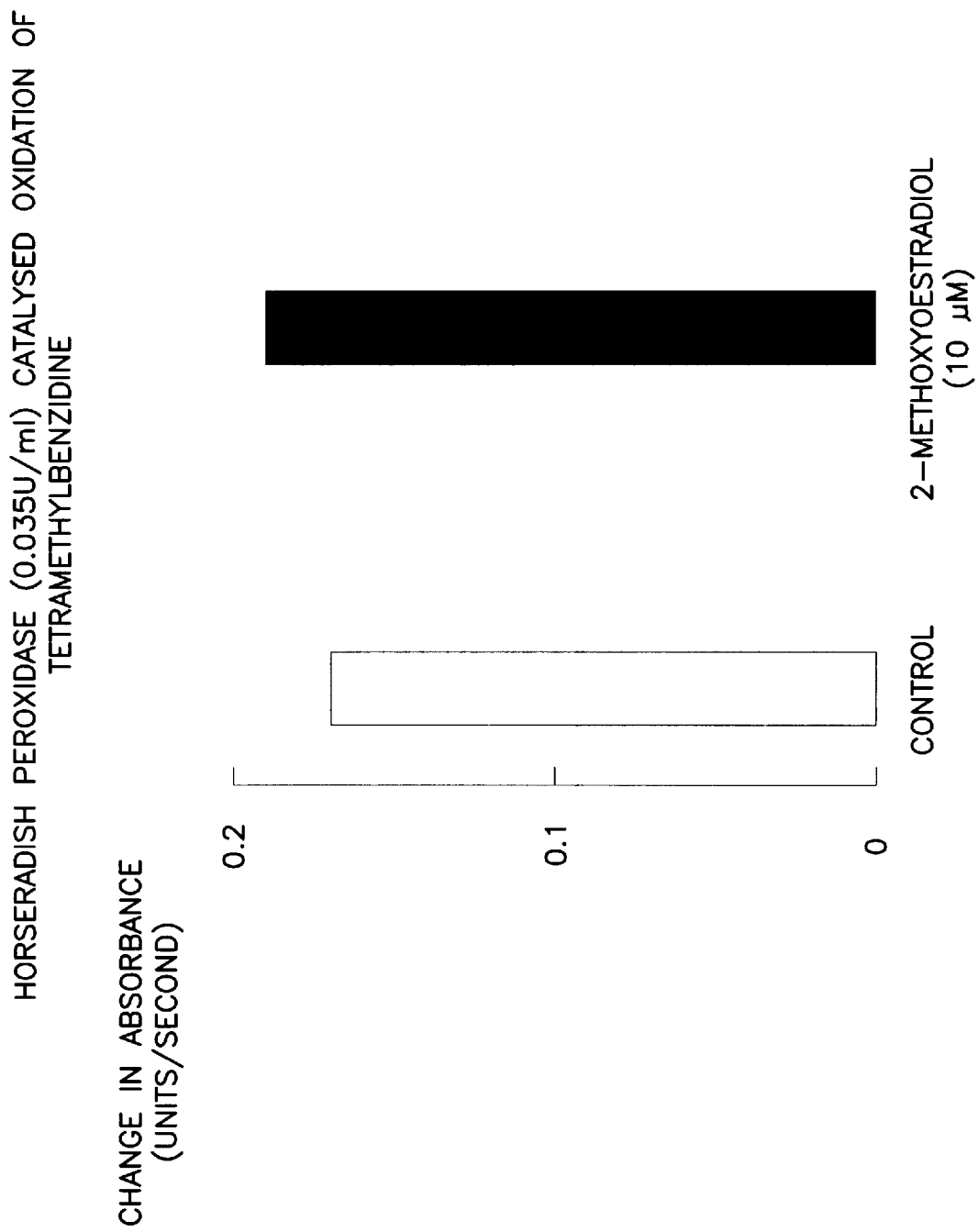
FIG. 1 shows the lack of effect of 2-methoxyoestradiol on horseradish peroxidase-medicated oxidation of tetramethyl benzidine.

Abbreviations used herein are as follows:

| | |
|---|---|
| AHR | airway hyperresponsiveness |
| bFGF | basic fibroblast growth factor |
| DNP-OA | dinitro-phenyol treated ovalbumin |
| EGF | epidermal growth factor |
| fMLP | formyl methiony leucyl Phenylalanine |
| PDGF | platelet-derived growth factor |
| PMA | phorbol myristate acetate |
| 5HT | serotonin |

General Methods
Cell culture

Human bronchial airway smooth muscle was obtained from macroscopically normal lung resection specimens from lung transplant donors or recipients provided by the Alfred Hospital (Melbourne). Cultures were prepared as previously described in detail (Tomlinson et al., 1994). Briefly, the tissue was partially digested in Dulbecco's Modified Eagle's Medium (DMEM), [supplemented with 2 mM L-glutamine, 100 μg/ml streptomycin, 100 U/ml penicillin-G, 2 μg/ml amphotericin B, and 0.25% w/v bovine serum albumin (BSA)] containing 3 mg/ml collagenase for 30 minutes at 37° C., and approximately 0.5 g smooth muscle was further digested by a 2 hour incubation in 0.5 mg/ml elastase, followed by an 18 hour incubation in collagenase (3 mg/ml) at 37° C. Cell suspensions were centrifuged (10 min, 100×g, 25° C.), washed three times in supplemented DMEM, resuspended in 25 ml DMEM containing 10% (v/v) heat-inactivated foetal calf serum (FCS), seeded into 25 cm$^2$ Falcon culture flasks and incubated (37° C., 5% $CO_2$) for 7 to 10 days until monolayer confluence was reached. Cells were then harvested weekly by 10 min exposure to 0.5% trypsin, 1 mM EDTA and passaged at a 1:3 split ratio into 75 cm$^2$ Falcon culture flasks. Cells at passage numbers 3 to 15 were used for experiments.

Immunocytochemistry

Cells were subcultured into 8-well glass tissue culture chamber slides (Labtek), and grown to 100% confluency in DMEM (10% FCS). Slides were washed three times in PBS, before fixation for 20 seconds in ice-cold acetone and stored for up to four weeks at 4° C. before staining. Following rehydration in PBS/BSA (0.25%) for twenty minutes, the cells were permeabilized by incubation in 0.5% Triton X-100 (in PBS) and incubated with primary antibody for at least 60 minutes at 22° C. The primary antibody was removed by washing 3 times with 0.25% BSA in PBS, and then the cells were exposed to the secondary antibody for at least 60 minutes at 22° C. (horseradish peroxidase (HRP)-conjugated goat anti-mouse; Ig F(ab')2 fragment or goat anti-rabbit IgG). Controls were provided by substituting the primary antibody for PBS/BSA (0.25%). The staining of the fixed cells was analysed by light microscopy (Olympus BH2 attached to a VideoPro 32 image analysis system, Faulding Imaging, Clayton, Victoria). The characteristics of the antibodies used to identify the smooth muscle in culture were established on native airway wall specimens. The antibodies used were raised against α-actin, myosin, calponin (all specific to smooth muscle), cytokeratin (epithelial cells) and PECAM-1 (CD31, which is a marker of endothelial cells).

The expression of smooth muscle α-actin, myosin and calponin was observed in all cultures used in this study. These cultures did not express detectable PECAM-1 staining, and less than 5% of the cells were positive for staining with the monoclonal antibody against cytokeratin. Paraffin-embedded sections of the airway adjacent to that used for generation of cultures stained positively for smooth muscle α-actin and myosin in bundles of airway smooth muscle and blood vessels only. The antibody against PECAM-1 stained vascular endothelium, whereas that against cytokeratin stained only the epithelium, confirming the specificity of these antibodies for the target antigens.

DNA and protein synthesis

Cells were subcultured into 24-well plates at a 1:3 ratio and allowed to grow to monolayer confluency over a 72–96 hour period in an atmosphere of 5% $CO_2$, in air at 37° C. The serum-containing medium was replaced with serum-free DMEM for a 24 hour period to produce growth arrest. In some experiments, the cells were pretreated with 2-methoxyoestradiol 30 min before the addition of mitogen. The stimulant (mitogen) was added to the appropriate wells together with a supplement containing insulin, transferrin, and selenium (Monomed A, 1% v/v). Monomed A was added to provide progression factors which are essential for the mitogenic activity of growth factors such as thrombin, epidermal growth factor (EGF) and basic fibroblast growth factor (bFGF) (Stewart et al., 1995a). Mitogens and inhibitors were left in contact with cells from the time of addition until the end of the experiment, unless indicated otherwise. Cells were incubated for 24 hours (37° C., 5% $CO_2$) before being pulsed with [$^3$H]-thymidine (1 μCi/ml for four hours) to measure incorporation of radiolabel into mely synthesized DNA, according to our previous study (Stewart et al., 1995).

Incorporation of radioactivity was determined by filtration at the end of the pulse-labelling period. The medium containing the radioactivity was aspirated and the cells were lysed by addition of 200 μl of 0.1 M NaOH. The DNA was immobilised by filtration in a binding harvester (Packard Filtermate 196) on glass fibre filters (Packard, standard), which were then washed with 3×3 ml volumes of distilled water and a single 1 ml volume of 100% ethanol. The dried filters were counted in a Packard Topcount liquid scintillation counter. Protein synthesis rates were determined in experiments of analogous design to those described above, but [$^3$H]-leucine replaced [$^3$H]-thymidine in the pulsing incubation of 4 hours. Furthermore, in experiments to determine the effects of mitogens and 2-methoxyoestradiol on the rate of protein synthesis, incubations with mitogen were carried out for a period of 48 hours. The longer duration of these experiments was required to allow sufficient time for cell division to occur.

Cell counting

The progression of airway smooth muscle cells through the cell-cycle to mitosis was determined by measuring changes in cell number in experiments of analogous design to those used for DNA sythesis, except that the incubations with mitogen were continued for 48 hours. Cells were removed from each of the wells of 6-well culture plates used in these experiments by exposure to 200 μl of 0.5% trypsin in PBS containing 1 mM EDTA, for a period of 30–45 min to ensure that the cells were completely dissociated from each other and from the culture plate to enable an accurate count to be made. At the end of this period, a further 200 μl of PBS (20% FCS) was added to prevent cell lysis by trypsin and cells were counted directly in a haemocytometer.

Statistical analyses

Each treatment in an individual experiment was carried out in quadruplicate for DNA and protein synthesis experiments. Each experiment was performed in at least three different cultures obtained from three different individuals. For cell counting, single incubations were carried out in three cultures. Results are presented as grouped data from multiple cultures and are expressed as mean ± S.E. of n cultures. The degree of increment was calculated by dividing the response of treated wells by that of the control wells on the same 24-well plate. The grouped data was analysed by paired t-test after normalisation by log transformation. The Bonferroni adjustment for multiple comparisons was used when necessary. Differenecs were considered to be significant when $p<0.05$.

Materials

All chemicals used were of analytical grade or higher. The compounds used and their sources were as follows: 2-methoxyoestradiol (1,3,5[10]-estratriene-2,3,17-triol 2-methylether lot 83H4065); 17β-oestradiol ((1,3,5[10]-estratriene-3, 17β-diol, cat no. E8876); 2-methoxyoestriol (1,3,5[10]-estratriene-2,3,16α, 17β-tetrol, lot 26F 4038; 2-methoxyoestrone, (2,3-dihydroxy 1,3,5[10]-estratriene-17-one, lot 110F4003), 2-hydroxyestradiol, (1,3,5[10]-estratriene-2,3,17β-triol lot 75H0853); L-glutamine, essentially fatty acid free bovine serum albumin fraction V (BSA), thrombin (bovine plasma), Sigma, USA; amphotericin B (Fungizone), human recombinant basic FGF (bFGF), Promega, USA; collagenase type CLS 1, elastase, Worthington Biochemical, USA; Dulbecco 'A' phosphate buffer saline (RBS), Oxoid, England; trypsin, versene, penicillin-G, Streptomycin, Monomed A, CSL, Australia, foetal calf serum (FCS), Flow Laboratories, Australia; Dulbecco's Modified Eagle's Medium (DMEM), Flow Laboratories, Scotland. [6-$^3$H]-thymidine (185GBq/mmol, 5 Ci/mmol), Amersham, UK; Microscint ~O scintillant, Canberra-Packard, Australia. The antibodies used for immunocytochemistry were anti-smooth muscle α-actin (mouse monoclonal) (Dako M851), monoclonal mouse anti-PECAM-1 (DAKO-CD31, JC/70A) (Dako M823), Dako Corporation, USA; anti-cytokeratin (mouse monoclonal CY90, Sigma, USA) anti-mouse Ig F(ab')2 fragment FITC-conjugate (host sheep), sheep anti-rabbit Ig HRP-conjugate (Silenus DDAF), Silenus, Australia, and anti-smooth muscle myosin (rabbit polyclonal), provided by Professor M Sparrow, Perth, Wash.

EXAMPLES 1

Effect of 2-methoxyoestradiol on Leucocyte Activity

Leucocyte activation is a feature of the pathology of asthma. The binding of 2-methoxyoestradiol to the colchicine binding site on tubulin raised the possibility that its this compound interferes with leukocyte functions such as phagocytosis and locomotion.

Functional effects of 2-methoxyoestradiol were examined on polymorphonuclear leukocytes (PMN) and adherent monocytes obtained from human peripheral blood. Superoxide anion generation was determined by superoxide dismutase-sensitive reduction of cytochrome C (Stewart & Harris, 1992). The release of myeloperoxidase was determined by oxidation of tertramethyl-benzidine (Menegazzi et al 1992). Phagocytosis was determined by radioidination of zymosan particles (Shelton & Hosking, 1975.

Guinea-pig peritoneal macrophages were harvested and cultured according to our previous studies (Stewart & Phillips, 1889). Cells were incubated with stimuli including the chemotactic tripeptide, formyl methiony leucyl Phenylalanine (fMLP, 100 nM), Zymosan (400 μg/ml) or phorbol myristate acetate (PMA, 100 nM) for 30 min in the presence or absence of 2-methoxyoestradiol (10 μM) added 15 min before the stimuli. Superoxide anion was determined by superoxide dismutase-sensitive reduction of cytochrome c (Stewart & Harris, 1992) and the stable metabolite of prostacyclin, 6-oxo-PGF1 was measured by radioimmunoassay (Stewart & Phillips, 1989). All individual incubations were carried out in duplicate and experiments were carried out in macrophages from 5 guinea-pigs.

RBL2H3 cells were cultured in RPMI 1640 containing 10% FCS and were passaged into 24 well plates for experiments. The cells were sensitised by a 48 hour incubation with 50% (V/V) conditioned medium from a lymphoid cell line secreting anti-DNP ovalbumin antibody. During the last 24 hours of this incubation [$^3$H]-5HT (1 μCi/ml) was added to each of the wells to label granular amine stores. At the end of the incubation period, the medium was aspirated, the cells were washed twice in RPMI 1640 and incubated in RPMI 1640 (0.25% BSA) in the absence or presence of 2-methoxyoestradiol for 15 mins prior to stimulation with DNP-treated ovalbumin, A23187 or PMA for 30 mins at which time the supernatants were harvested, subjected to centrifugation (1000×g, 4° C., 5 min) and aliquots taken for determination of the amount of [$^3$H]-5HT released. All experiments were carried out in quadruplicate.

The results showed that 2-methoxyoestradiol (3 μM) reduced oxidation of tetramethyl-benzidine in leukocytes stimulated with either zymosan (400 μg/ml) or fMLP, as shown in Table 1. Cell-free supernatants from fMLP stimulated leukocytes also contained myeloperoxidase activity as determined by tetramethyl-benzidine oxidation, but this activity was reduced only by the highest concentration of 2-methoxy-oestradiol (10 μM). In addition, experiments were carried out to examine whether there was a direct effect of 2-methoxyoestradiol on oxidation of tetramethyl benzidine by purified horseradish peroxidase. 2-methoxyoestradiol (10 μM) had no effect in this assay. Results are summarised in FIG. 1.

TABLE 1

Tetramethylbenzidine oxidation by Human polymorphonuclear leukocytes

|  | Control | fMLP 100 nM | Zymosan 400 μg/ml |
|---|---|---|---|
| Basal | −0.001± 0.002 | 0.057± 0.021 | 0.26± 0.009 |
| 2-methoxy-estradiol 3 μM | −0.004± 0.001 | 0.028± 0.03 | 0.013± 0.012 |

Data are expressed as change in absorbance value. Assays were carried out using $2\times10^6$ PMN in 0.5 ml buffer.

In PMN, superoxide anion generation in response to fMLP (100 nM) or zymosan (400 μg/ml) was not reduced by concentrations of 2-methoxyoestradiol up to 10 μM. In phagocytosis experiments, radioiodination of zymosan particles by PMN was reduced by 2-methoxyeostradiol with significant effects being observed at both 3 and 10 μM, as shown in Table 2.

TABLE 2

$^{125}$I uptake by Human polymorphonuclear leukocytes.

|  | No PHS | | PHS* | |
|---|---|---|---|---|
|  | Control | Zymosan | Control | Zymosan |
| Basal | 1.80± 0.09 | 2.83± 0.09 | 2.13± 0.24 | 4.33± 0.51 |
| 2-methoxy-oestradiol 3 μM | 1.97± 0.44 | 1.97± 0.48 | 1.87± 0.46 | 3.27± 0.64 |
| 2-methoxy-oestradiol 10 μM | 2.05± 0.44 | 1.80± 0.49 | 1.75± 0.45 | 1.65± 0.15 |

*PHS = pooled human serum
Data are expressed as percentage of $^{125}$I incorporation into glass fibre-filterable material. Assays were carried out using $1 \times 10^6$ PMN.

In adherent monocytes the oxidation of tetramethyl benzidine in respone to phorbol myristate acetate (1 μM) PMA or zymosan (400 μg/ml) was unaffected by 10 μM 2-methoxyoestradiol. Furthermore, superoxide anion generation in response to PMA was also unaffected in this cell type. However, zymosan-stimulated superoxide anion generation appeared to be markedly inhibited by 2-methoxyoestradiol (10 μM) in monocytes from at least some donors.

Figure 8:
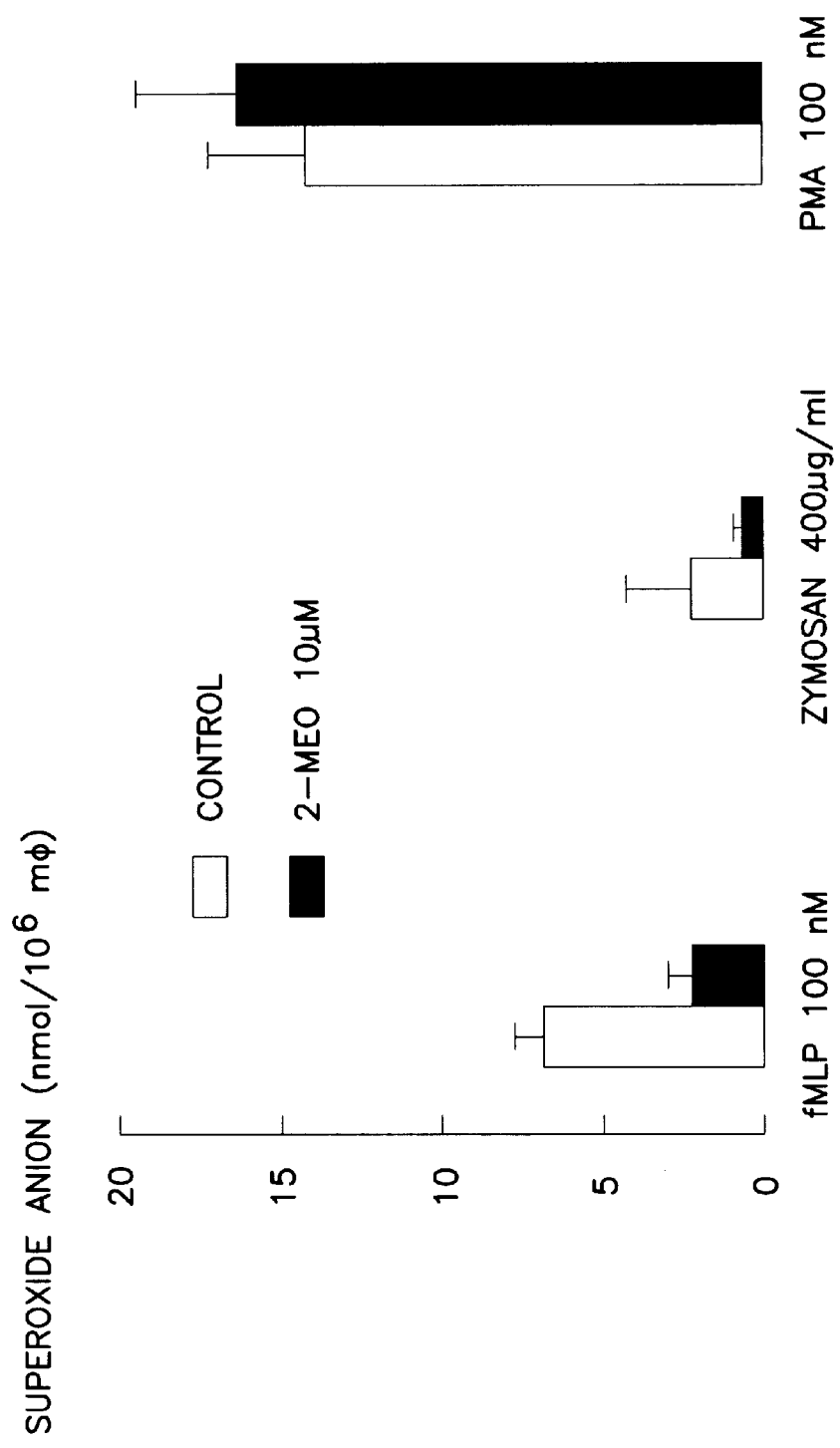
FIG. 8 shows the effect of 2-methoxyoestradiol on superoxide anion release in guinea-pig peritoneal macrophages. This compound completely blocked superoxide anion response of the macrophages to zymosan and reduced those to fMLP.
Figure 9:
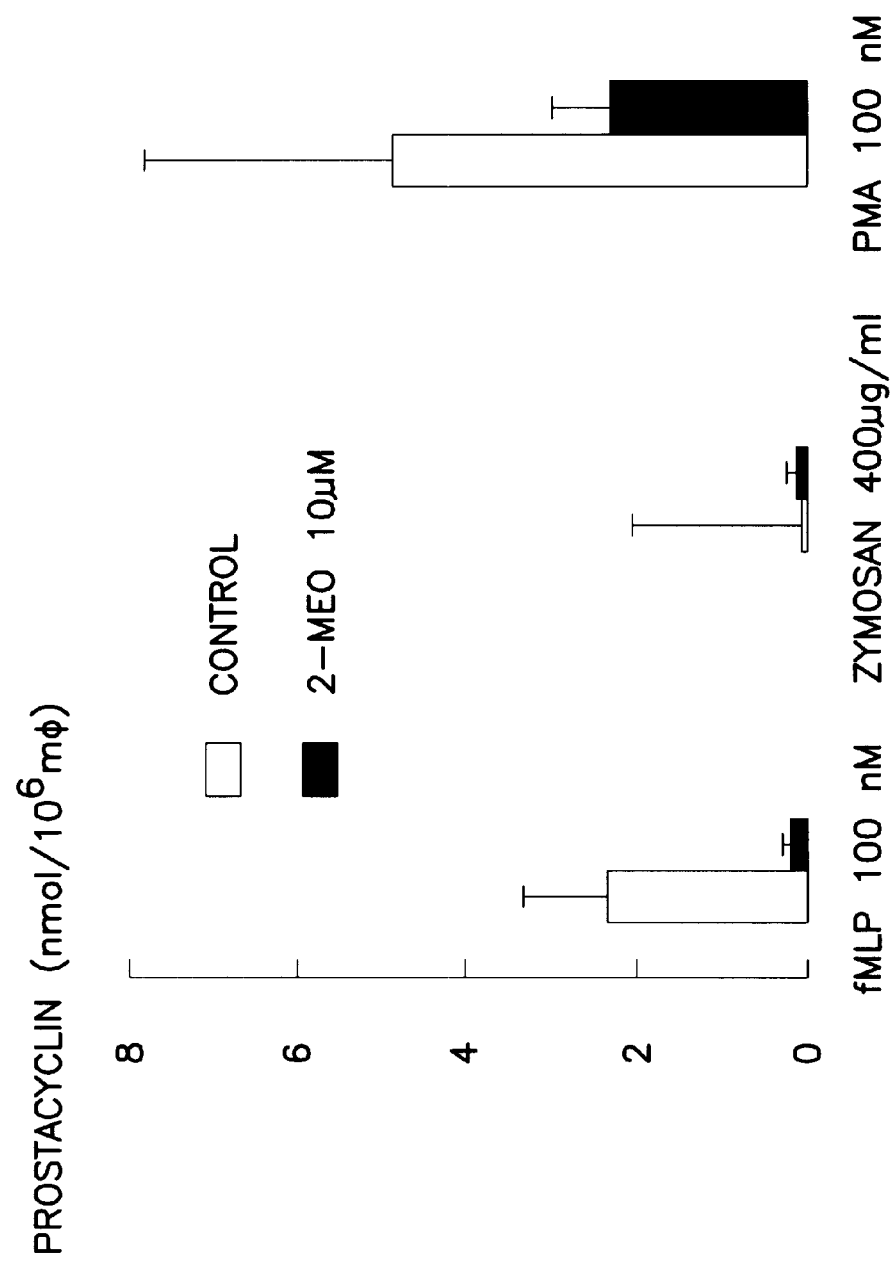
FIG. 9 shows the effect of 2-methoxyoestradiol on prostacylin release in guinea-pig peritoneal macrophages. The results demonstrate that the estradiol completely blocked the macrophage response to fMLP whilst the response to PMA was inhibited by 50%.

The superoxide anion response of guinea-pig macrophages to zymosan or fMLP was reduced by 2-methoxyoestradiol as shown in FIG. 8. However, the response to PMA (100 nM) was unaffected. In addition, fMLP (100 nM)-induced increases in 6-oxo-PGF1 αgeneration were completely blocked by 2-methoxyoestradiol, whereas the response to PMA was reduced by only 50%, and zymosan did not stimulate an increase in the levels of the prostacyclin metabolite as shown in FIG. 9.

Figure 10:
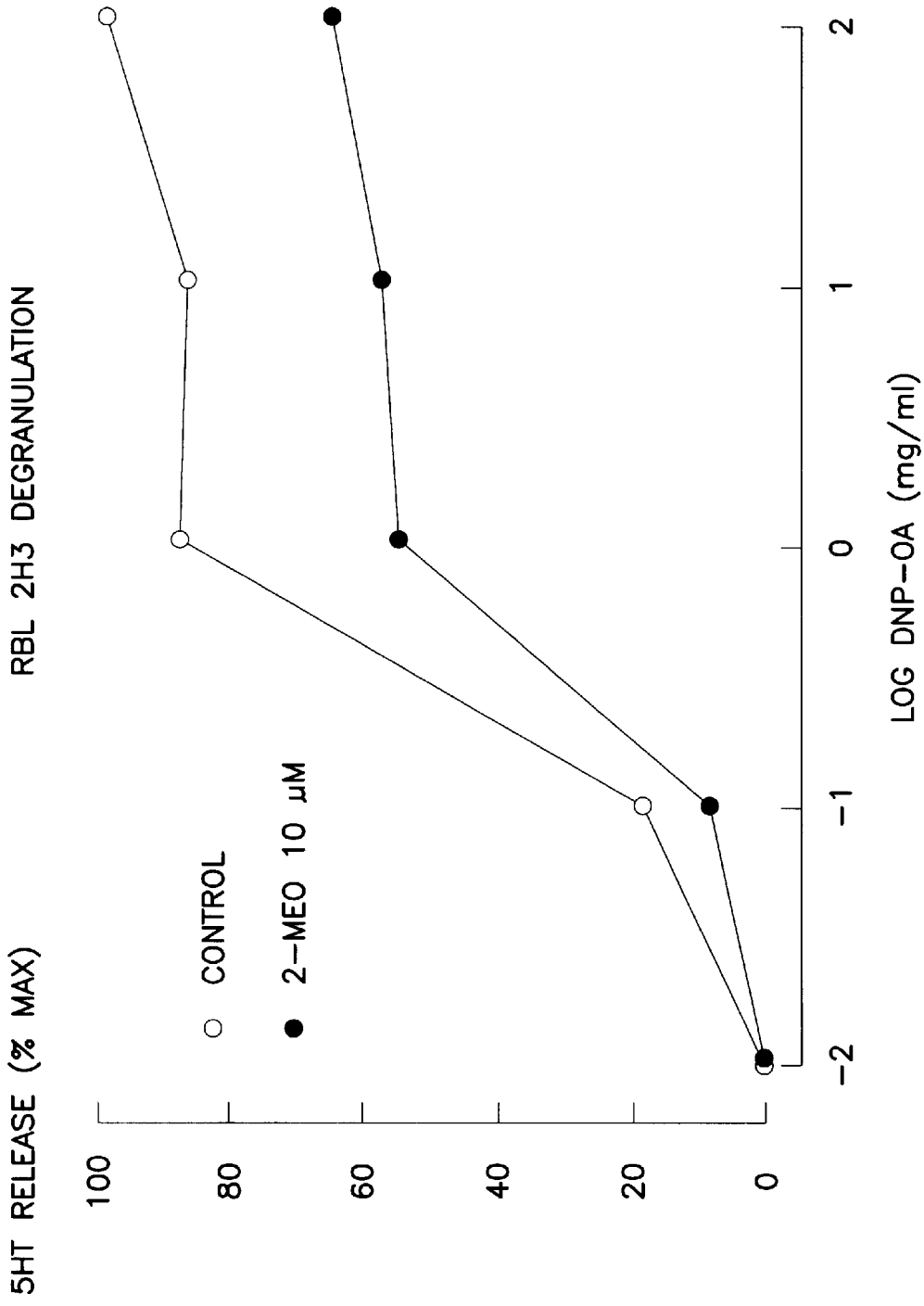
FIG. 10 is a plot showing the effects of various concentrations of ovalbumin (DNP-OA) on mast cell (RBL2H3) degranulation, and the inhibition by 2-methoxyoestradiol.
Figure 11:
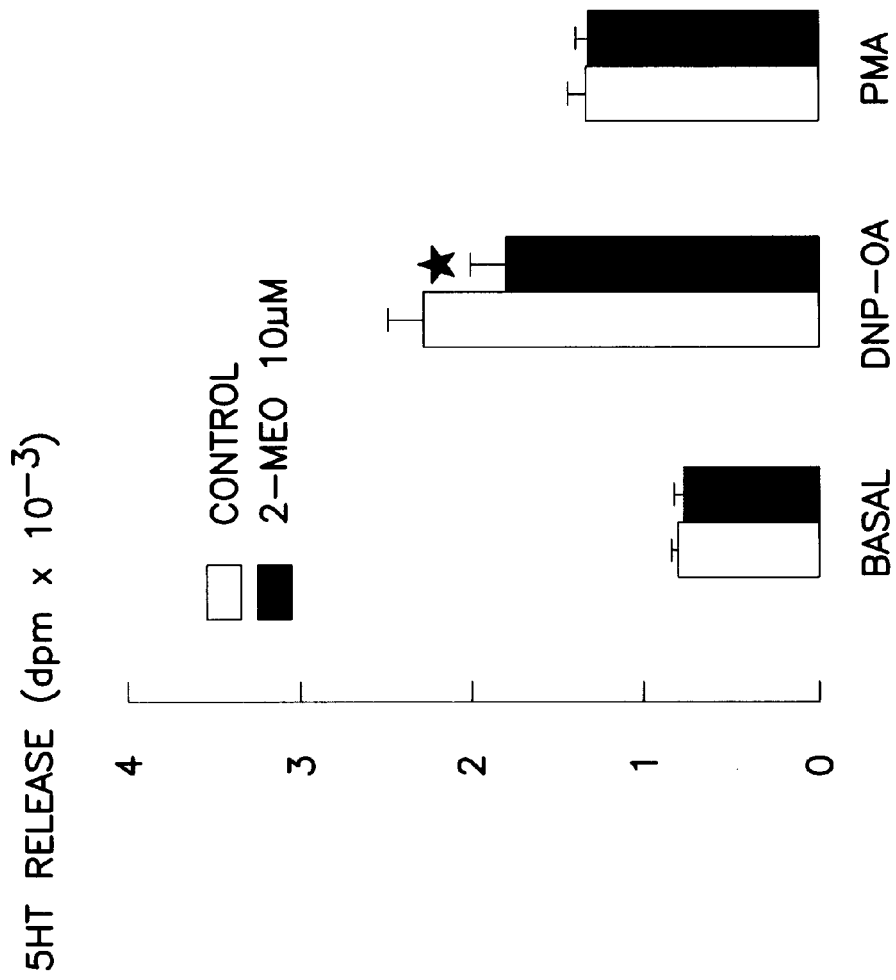
FIG. 11 shows that 2-methoxyoestradiol reduced ovalbumin (DNP-OA)-stimulated release of [$^3$H]-5HT from guinea-pig peritoneal macrophages, but did not affect release in response to PMA.

Ovalbumin (DNP-OA) elicited a concentration-dependent release of [$^3$H]-5HT which was reduced by 10 μM 2-methoxyoestradiol as can be seen in FIG. 10. However, the basal release of [$^3$H]-5HT and that in response to either PMA (100 nM) or the calcium ionophone A23187 (10 μM) were unaffected by 2-methoxyoestradiol as shown in FIG. 11.

The inhibitory effects of 2-methoxyoestradiol on PMN myeloperoxidase release and activity, together with the reduction in phagocytosis, indicate that the compound will have an anti-inflammatory effect in vivo. The selective inhibition of zymosan-stimulated superoxide anion generation suggests a specific effect on this phagocytic stimulus. These observations and our experiments showing inhibitory effects on macrophage function provide clear evidence of anti-inflammatory properties of benefit in asthma and other chronic obstructive airways diseases, particularly those with demonstrable PMN involvement.

EXAMPLE 2

Effect of 2-methoxyoestradiol on DNA Synthesis

Figure 2A:
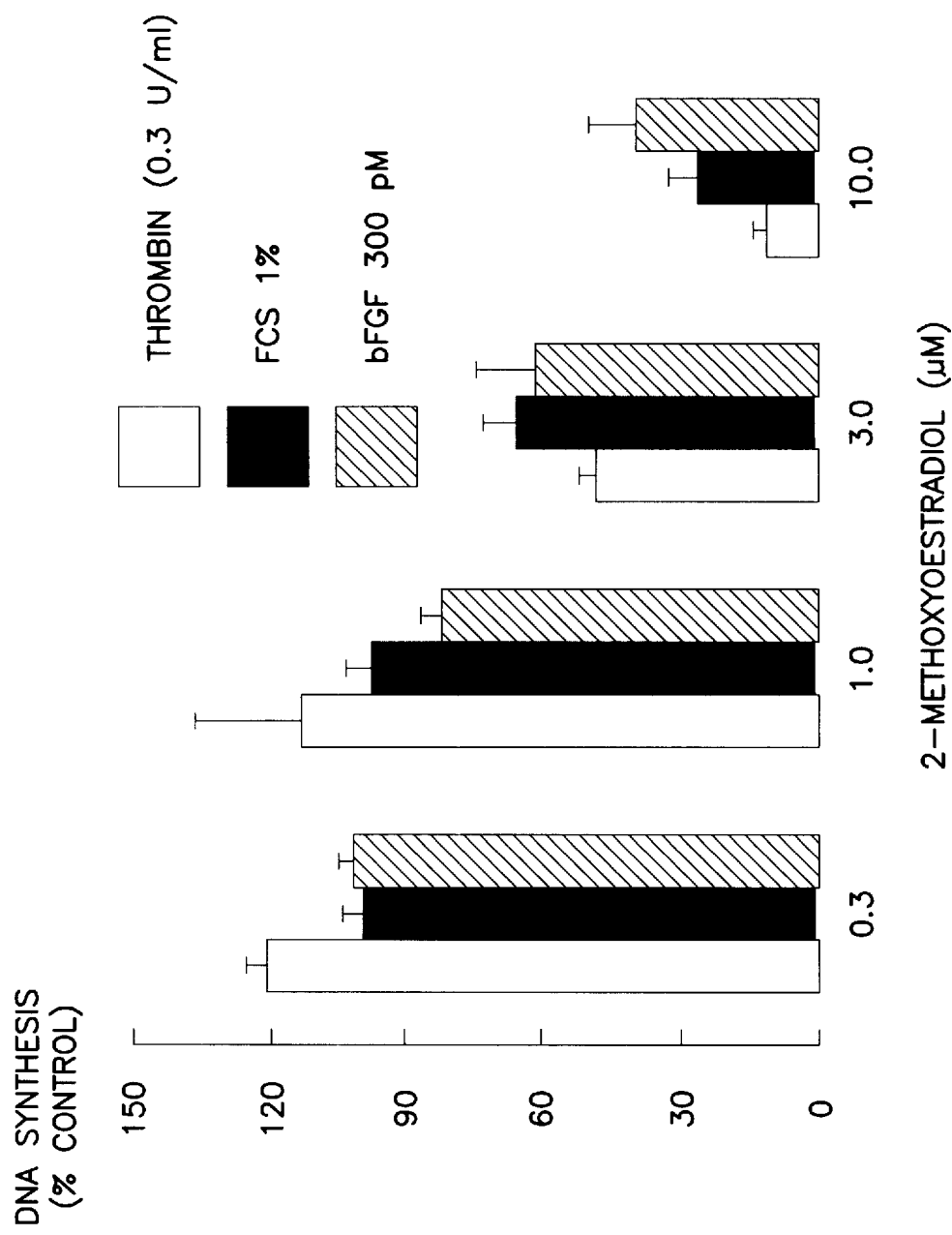
FIG. 2 shows the effect of 2-methoxyoestradiol (0.3–10 $\mu$M, 30 min pretreatment) on mitogen-induced incorporation of [$^3$H]-thymidine in cultured human airway smooth muscle cells. Mitogens tested were 0.3 U/ml Thrombin, 1% FCS, 300 pM bFGF (FIG. 2a) and 10% FCS, 3 nM EGF (FIG. 2b). Additional experiments of identical design to those depicted in FIGS. 2a & b were carried out and the combination of this latter data and that in FIGS. 2a & b is presented in FIG. 2c. The time-course of the effect of 2-methoxyoestradiol (3 $\mu$M) on thrombin (0.3 U/ml)-induced DNA synthesis were also investigated (2d). Data are presented as the means and standard errors of the means of 3 experiments in 3 different cultures, and are expressed as a percentage of the [$^3$H] -thymidine incorporation in non-pretreated cells.
Figure 2B:
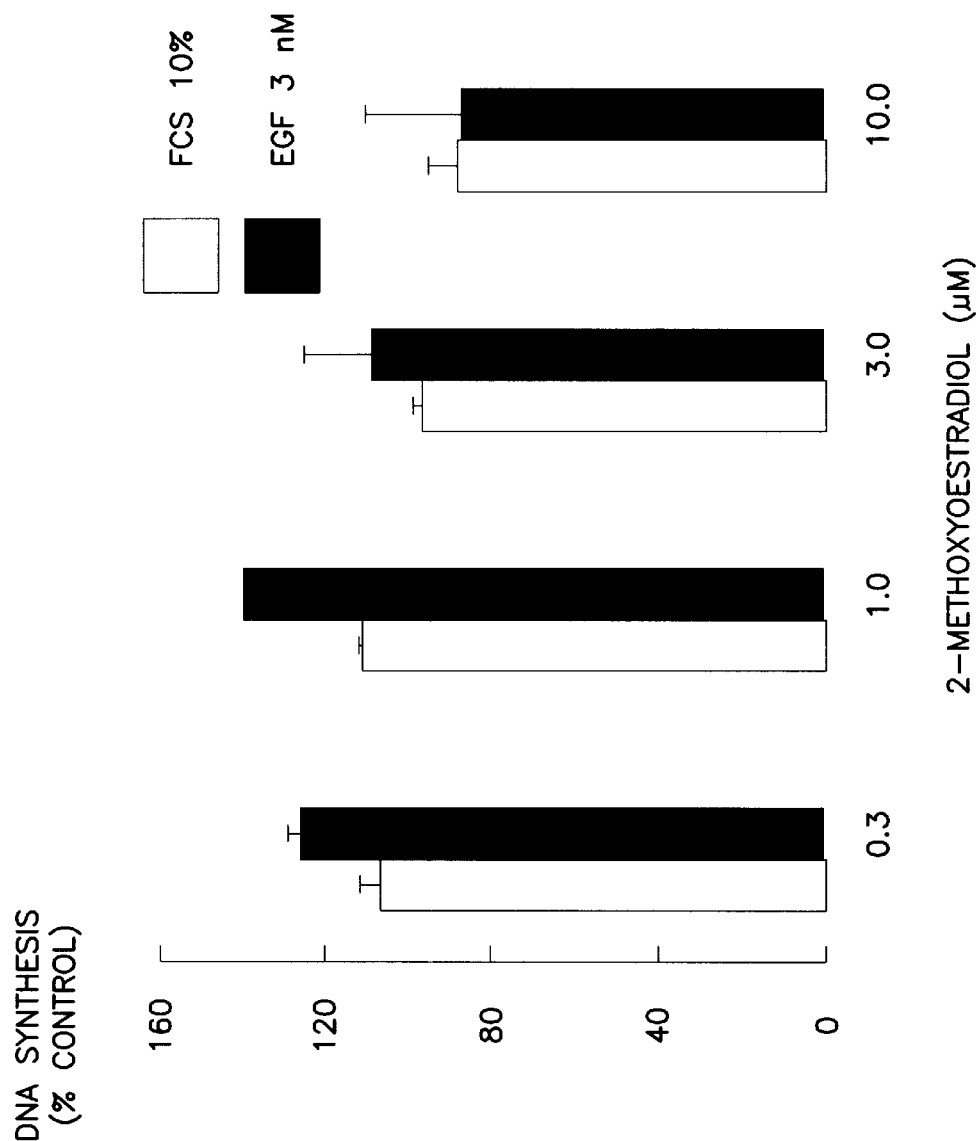
Figure 2C:
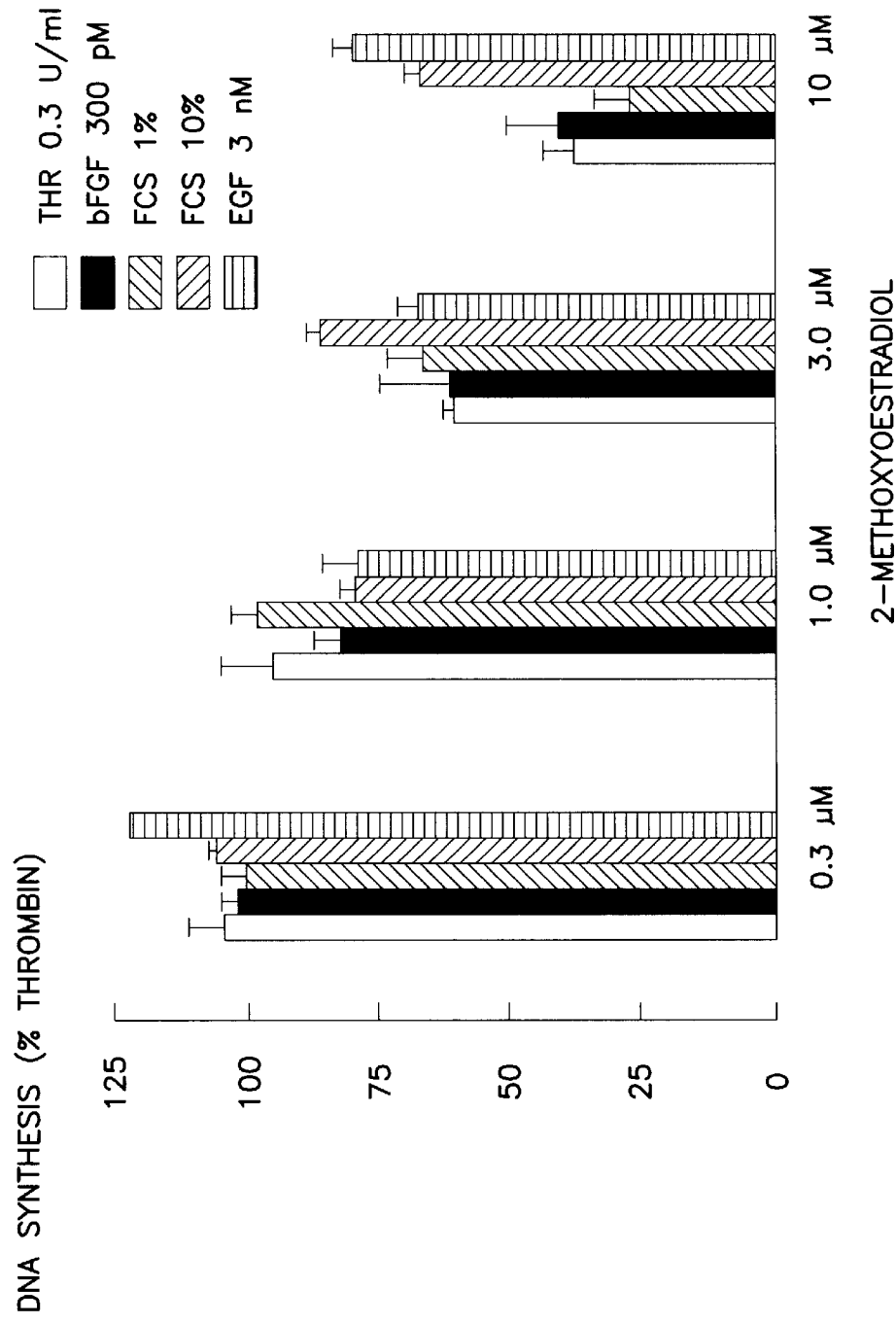

Incubation of human cultured airway smooth muscle cells with 0.3–10 μM of 2-methoxyoestradiol for 30 min before mitogen addition, and throughout the remaining 28 hours of the experiment, caused a concentration-dependent reduction in thrombin (0.3 U/ml)-stimulated incorporation of [$^3$H]-thymidine, as shown in FIG. 2a. At the highest concentration of 2-methoxyoestradiol used (10 μM), the response to thrombin was reduced to approximately 10% of the control level. This inhibitory effect of 2-methoxyoestradiol on DNA synthesis was not restricted to the presence of thrombin, as similar concentration-related inhibitory effects of 2-methoxyoestradiol were observed in cells in which DNA synthesis was stimulate with either foetal calf serum (FCS, 1% v/v) or basic fibroblast growth factor (bFGF, 300 pM) (FIGS. 2a and 2b. However, DNA synthesis in the presence of either EGF (3 nM) or 10% FCS was inhibited to a significantly lesser extent than responses to thrombin, bFGF or lower concentrations of FCS (FIG. 2c). The DNA synthesis in response to 10% FCS (27.2±7.8 times more than the unstimulated level of [$^3$H]-thymidine incorporation) was significantly greater (p<0.05, paired Student's t-test) than the response to 0.3 U/ml thrombin (8.4±3.1 fold), 3 nM EGF (4.5±0.7) or 1% FCS (12.7±0.4), but not significantly different from the response to 300 pM bFGF (22.5±5.3).

Figure 2D:
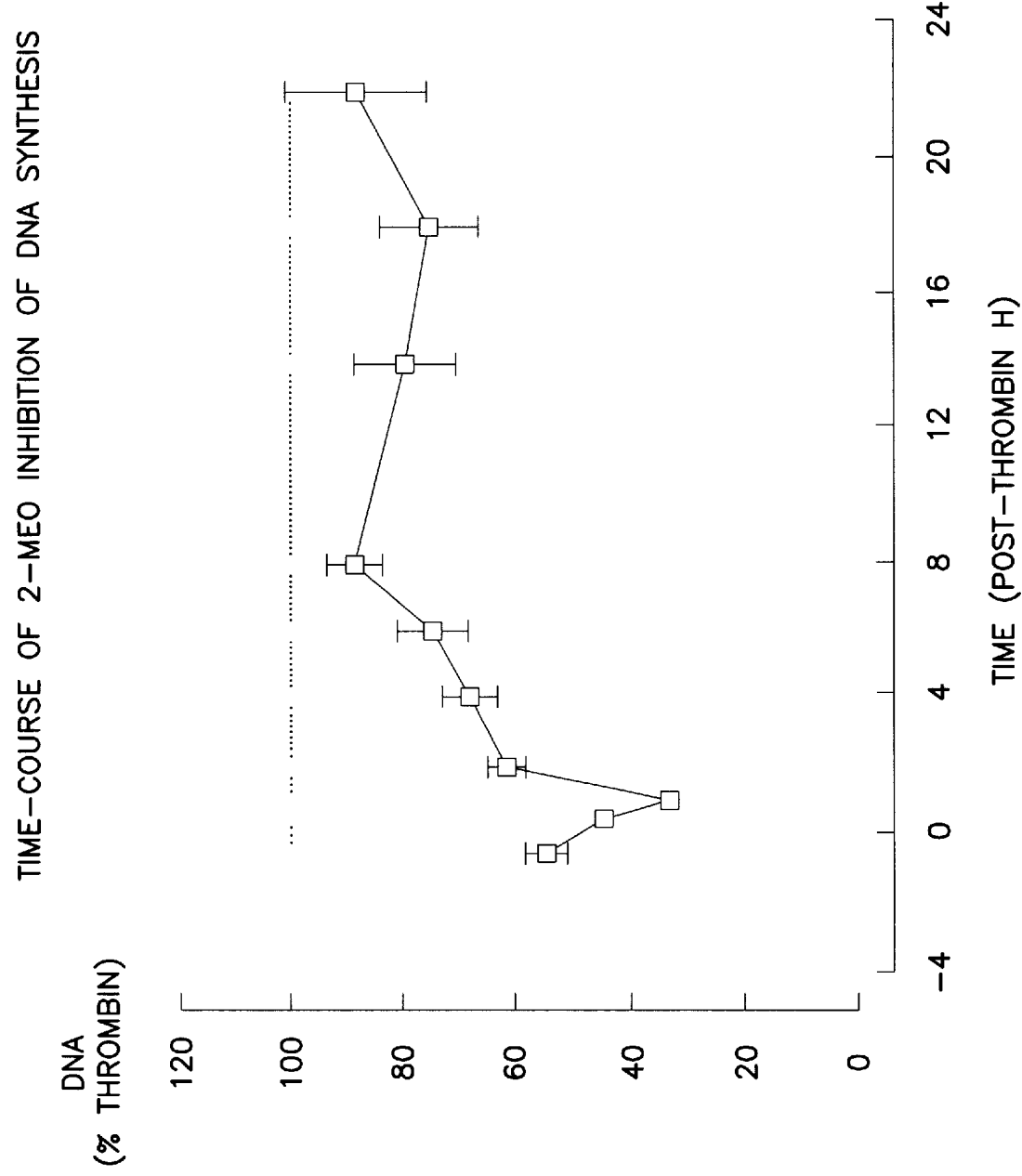

Time-course studies were also carried out to determine whether addition of 2-methoxyoestradiol, after exposure to mitogens, still inhibited DNA synthesis. Thrombin (0.3 U/ml)-stimulated DNA synthesis was inhibited when 2-methoxyoestradiol (3 μM) was added up to 4 hours after the thrombin, with maximum inhibition being observed at 2 hours after thrombin addition. Addition of 2-methoxyoestradiol between 4 and 14 hours after the thrombin resulted in a small inhibition (~20%), whereas addition at 18 hours or later had no effect on the DNA synthesis in the presence of this mitogen as shown in FIG 2d. Subsequently, additional time points were examined and these studies indicated that the highest level of activity was observed when 2-methoxyoestradiol was added either simultaneously or 1 hour after thrombin, but significant inhibition persisted up to 6 hours after thrombin addition (FIG. 2d).

EXAMPLE 3

Effect of 2-methoxyoestradiol on protein synthesis and cell numbers

Figure 3:
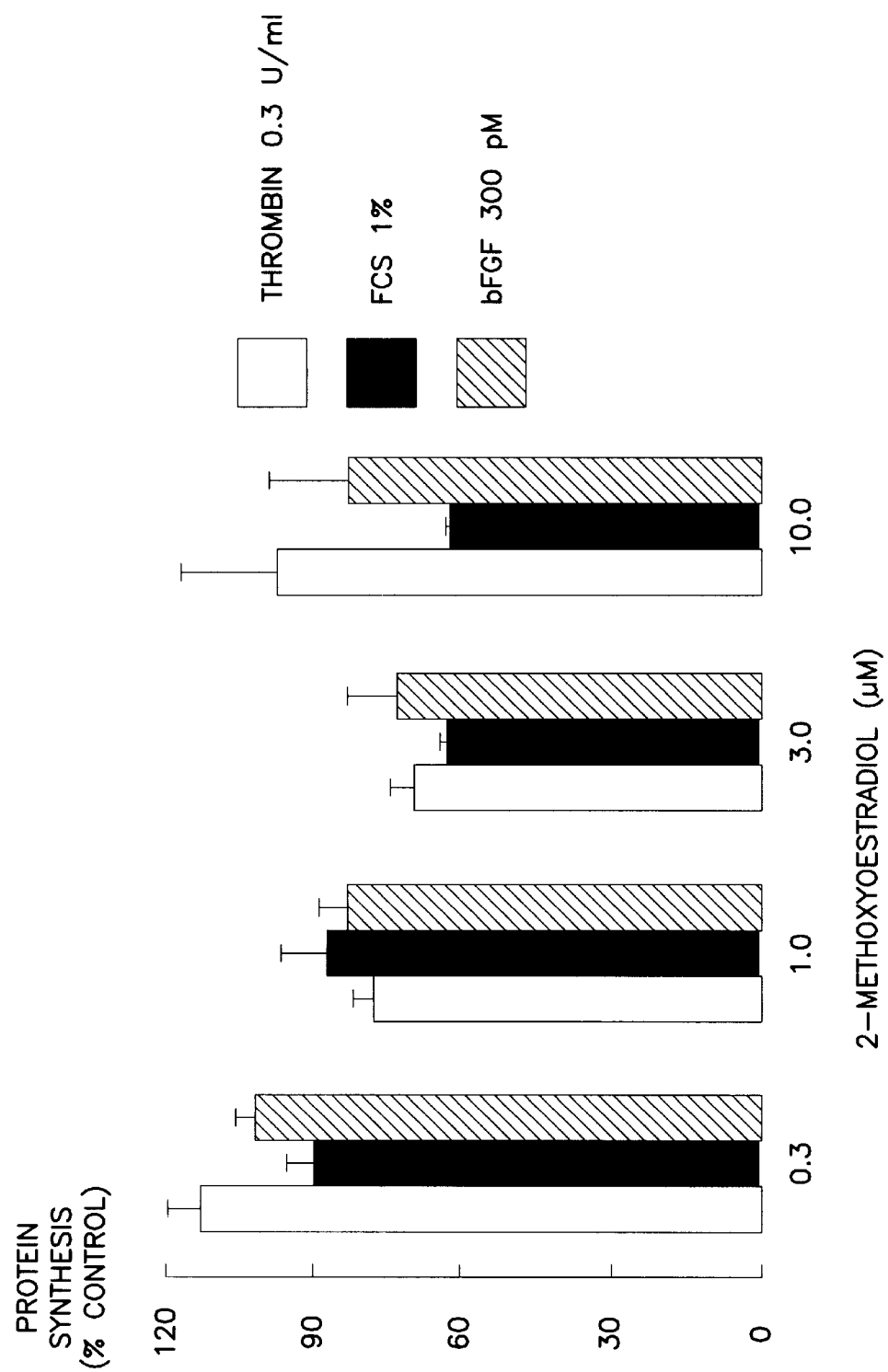
FIG. 3 shows the effect of 2-methoxyoestradiol (0.3–10 $\mu$M, 30 min pretreatment) on mitogen-induced incorporation of [$^3$H]-leucine. Data are presented as the means and standard errors of the means of 3 experiments in 3 different cultures, and are expressed as a percentage of the [$^3$H]-leucine incorporation in non-pretreated cells.
Figure 4A:
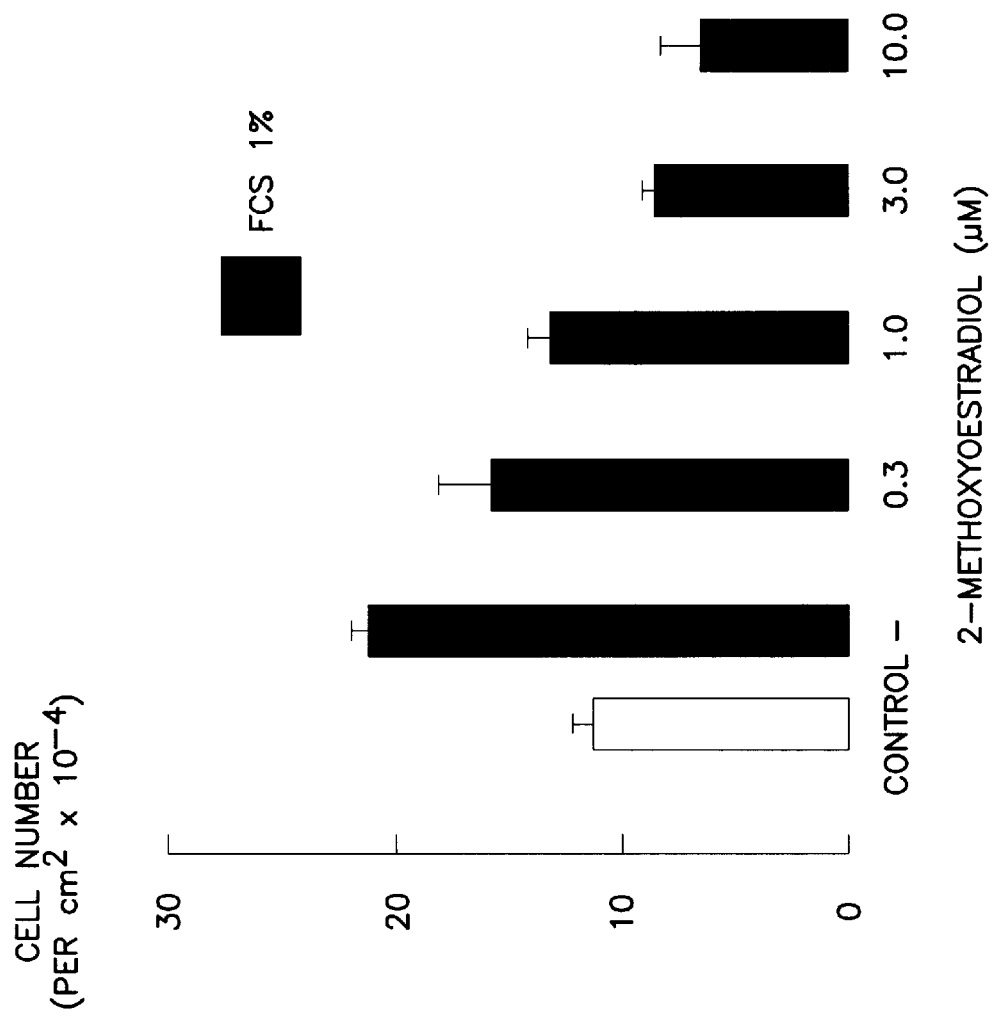
FIG. 4 shows the effect of 2-methoxyoestradiol (0.3–10 $\mu$M, 30 min pretreatment) on cell number in the presence of (a) FCS (1%) or (b) bFGF (300 pM). Data are presented as the means and standard errors of the means of 3 experiments in 3 different cultures, and are expressed as a percentage of the increase in cell number in non-pretreated cells.
Figure 4B:
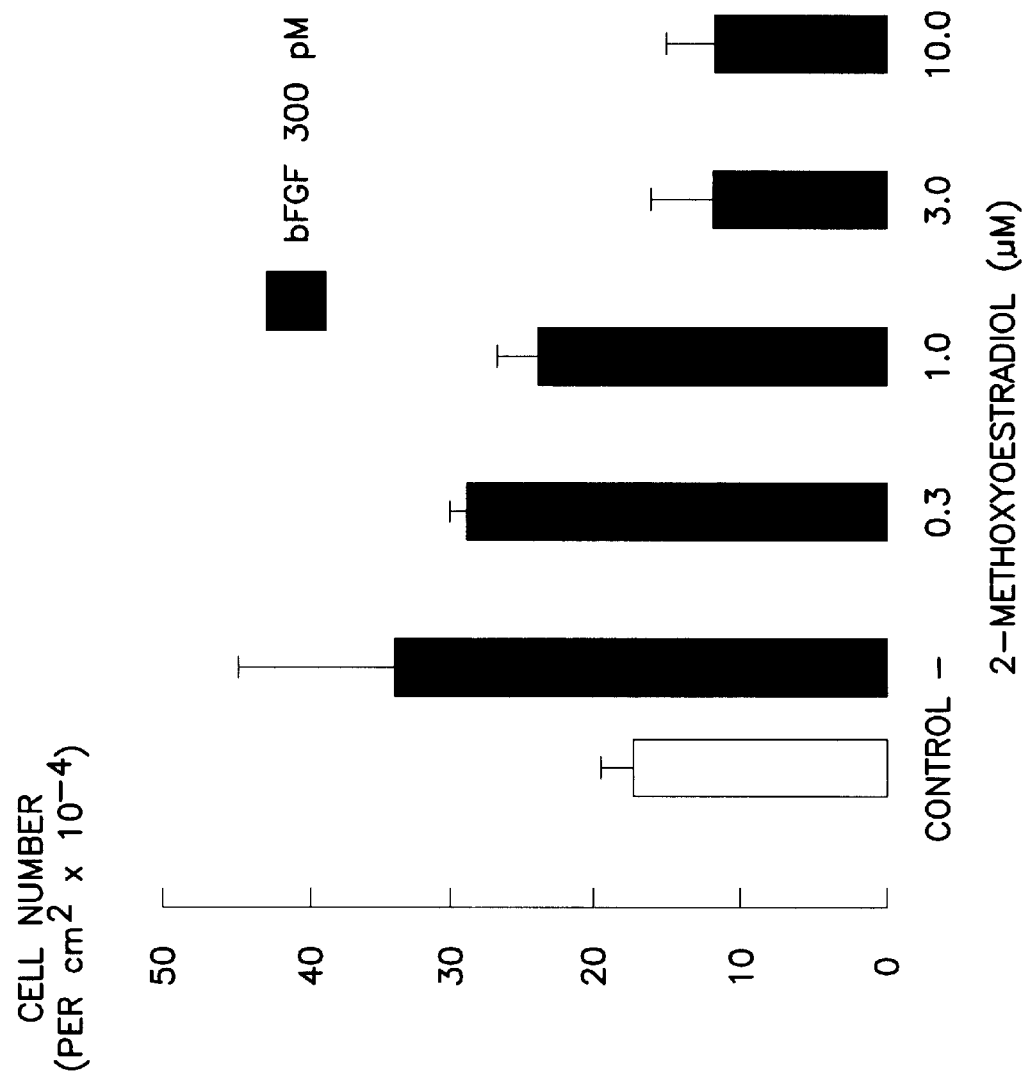

In order to determine whether inhibition of DNA synthesis also resulted in arrest of cell-cycle progression and inhibition of mitosis, measurements of both protein synthesis and cell numbers after 48 hours of incubation with mitogens were made. The threshold concentration for inhibition of incorporation of [$^3$H]-leucine in the presence of thrombin (0.3 U/ml), FCS (1% v/v) or bFGF (300 pM) was 1 μM, and was similar to the results for inhibition of [$^3$H]-thymidine incorporation. The maximum percentage reduction of the response of approximately 30% was less than the value observed with DNA synthesis, and occurred at 3 μM. At 10 μM, there was no significant inhibitory effect in the presence of thrombin or bFGF, as shown in FIG. 3. 2-methoxyoestradiol alone caused a small stimulation of [$^3$H]-leucine incorporation at 0.3 μM. Higher concentrations (1 and 3 μM) had small inhibitory effects and at 10 μM there was no effect. These results are summarised in Table 3. In contrast, the increases in cell number in response to either FCS (1%, v/v) or bFGF (300 pM) were more sensitive to inhibition by 2-methoxyoestradiol than either protein or DNA synthesis, with complete inhibition of the proliferation responses being observed at 3 μM as shown in FIGS. 4a and b.

TABLE 3

Effect of 2-methoxyoestradiol on protein synthesis rates in unstimulated smooth muscle cells.

| 2-methoxy-oestradiol (μM) | [$^3$H]-leucine incorporation (% control) mean ± SEM |
|---|---|
| — | 100 |
| 0.3 | 135 ± 3* |
| 1.0 | 84 ± 4* |
| 3.0 | 77 ± 3* |
| 10.0 | 113 ± 9 |

*p < 0.05 paired Student's t-test, compared to 100% (no pretreatment)

EXAMPLE 4

Serotonin-stimulated [$^3$H]-leucine incorporationj in Smooth Muscle Cells.

Serotonin (5HT) at concentrations from 0.1 nM up to 10 μM had no effect on incorporation of [$^3$H]-thymidine, but 10 nM 5HT increased incorporation of [$^3$H]-leucine. Preincubation with 0.3–10 μM of 2-methoxyoestradiol decreased the 5HT (10 nM)-stimulated increase in protein synthesis in a concentration-dependent manner, as summarized in Table 4.

TABLE 4

Effect of 2-methoxyoestradiol on protein synthesis rates in 5HT-stimulated smooth muscle cells.

| 2-methoxy-oestradiol (μM) | [$^3$H]-leucine incorporation (% control) mean ± SEM |
|---|---|
| — | 100 |
| 0.3 | 91 ± 5 |
| 1.0 | 62 ± 2* |
| 3.0 | 56 ± 2* |
| 10.0 | 51 ± 6* |

*p < 0.05 paired Student's t-test, compared to 100% (no pretreatment)

EXAMPLE 5

Morphological effects of 2-methoxyoestradiol

Figure 5:
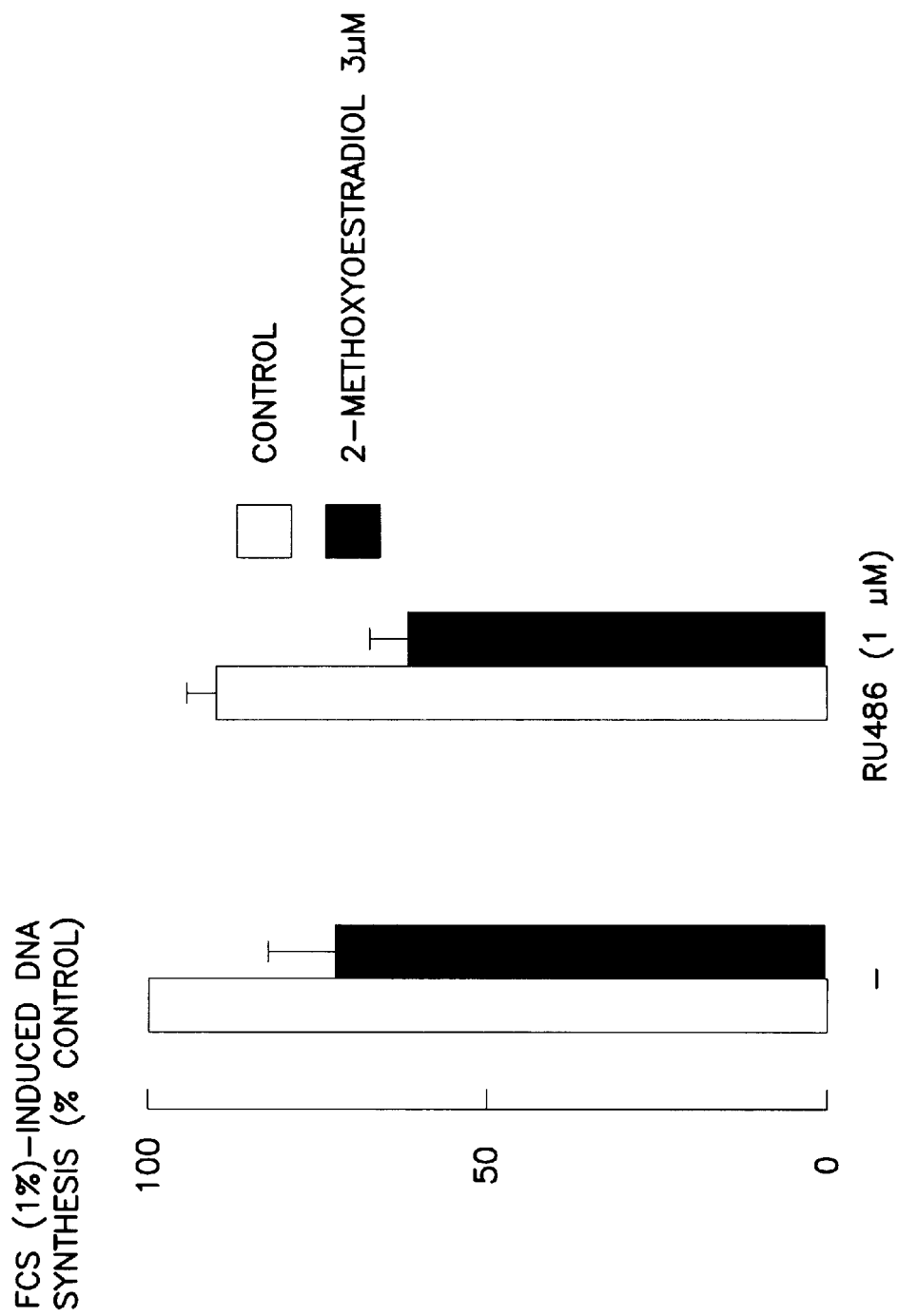
FIG. 5 shows the effect of the steroid receptor antagonist, RU 486 (1 $\mu$M), on 2-methoxyoestradiol (3 $\mu$M) inhibition of FCS (1%)-induced DNA synthesis. Data are presented as the means and standard errors of the means of 3 experiments in 3 different cultures, and are expressed as a percentage of the [$^3$H]-thymidine incorporation in non-pretreated cells. RU 486 was added 30 min before 2-methoxyoestradiol, which was added 30 min before FCS.

Morphological changes including the manifestation of a rounded appearance of the normally spindle-shaped cells were observed at concentrations of 3 and 10 μM of 2-methoxyoestradiol. The shape changes were relatively rapid in onset, being observed within 6 hours, and were maintained for the duration of the incubation. These shape changes were similar to those elicited by incubation of cells with the microtubule disaggregating agent, colchicine (0.1–10 μM). The steroid receptor antagonist, RU 486 [Stewart et al., 1995b] reduced the shape changes in response to either colchicine or 2-methoxyoestradiol, but had no effect on the inhibition of DNA synthesis by 2-methoxyoestradiol. These results are illustrated in FIG. 5.

EXAMPLE 6

Effects of analogues of 2-methoxyoestradiol

Figure 6:
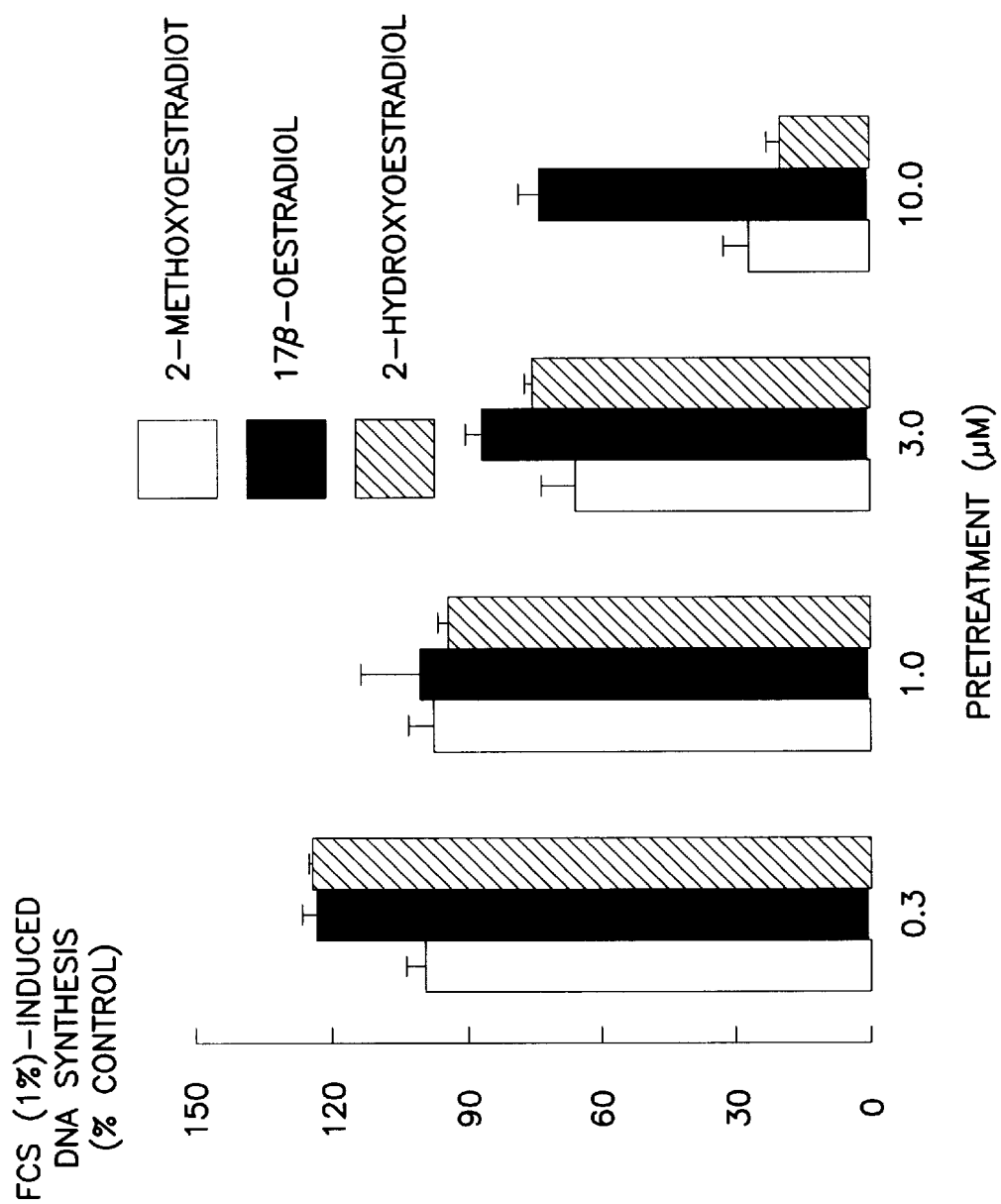
FIG. 6 shows the effect of 17β-oestradiol and 2-hydroyoestradiol (0.3–10 μM, 30 min pretreatment) on FCS (1%)-induced incorporation of [$^3$H]-thymidine. Data are presented as the means and standard errors of the means of 3 experiments in 3 different cultures, and are expressed as percentage of the [$^3$H]-thymidine incorporation in non-pretreated cells. Data relating to 2-methoxyoestradiol are reproduced from FIG. 1 for ease of comparison.
Figure 7:
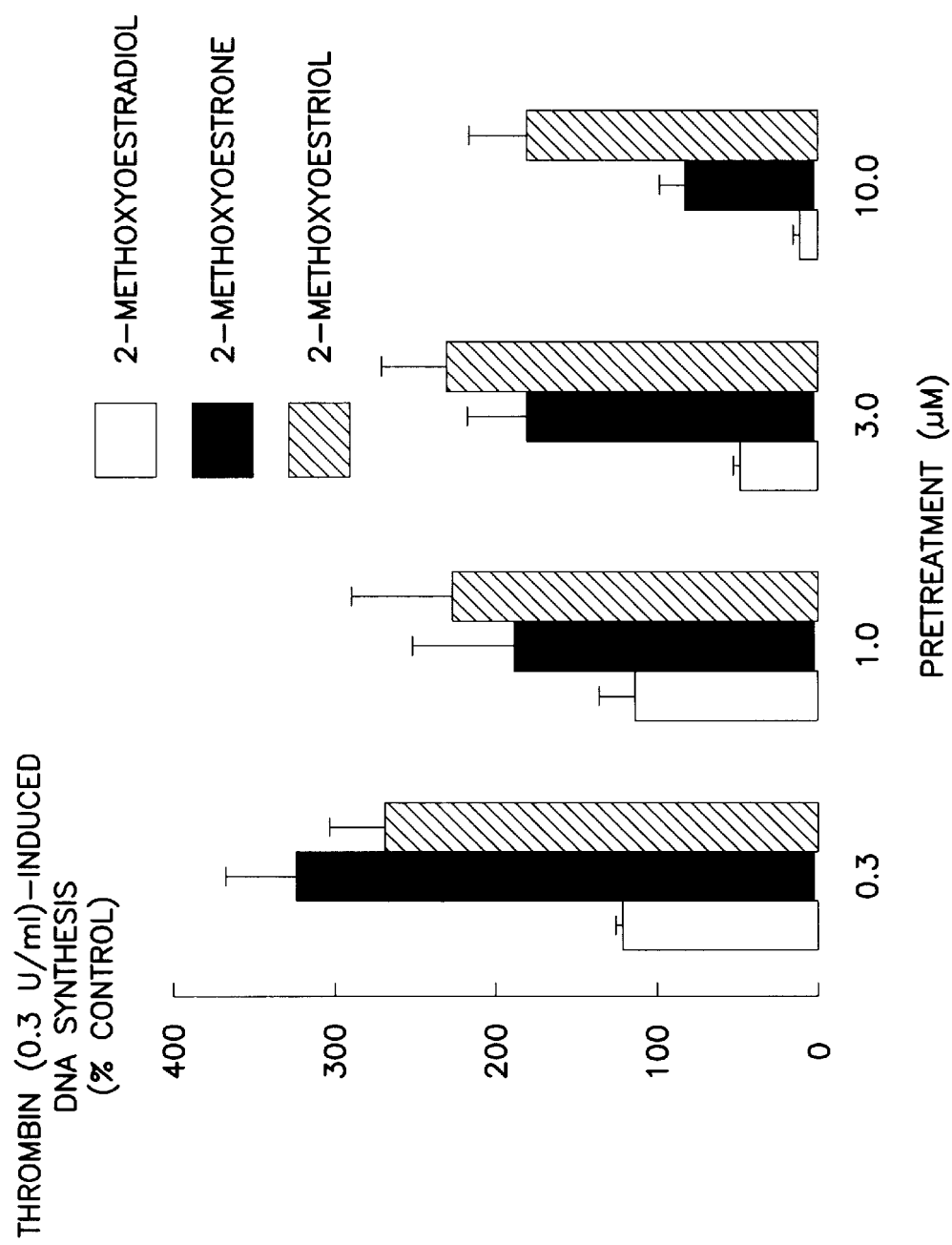
FIG. 7 shows the effects of 2-methoxyoestrone and 2-methoxyoestriol (0.3–10 μM, 30 min pretreatment) on thrombin (0.3 U/ml)-induced incorporation of [$^3$H]-thymidine. Data are presented as the means and standard errors of the means of 3 experiments in 3 different cultures, and are expressed as a percentage of the [$^3$H]-thymidine incorporation in non-pretreated cells. Data relating to 2-methoxyoestradiol are reproduced from FIG. 2a for ease of comparison.

Several compounds related to 2-methoxyoestradiol were examined for inhibition of FCS (1%, v/v)-stimulated DNA synthesis, including the parent compound, 17β-oestradiol, and the immediate precursor, 2-hydroxyoestradiol. The lower concentrations of each of these compounds enhanced FCS (1%)-stimulated DNA synthesis, as shown in FIG. 6. At higher concentrations, the enhancement was reversed, and inhibition was observed at 10 μM of these compounds. The inhibitory effect of 2-hydroxyoestradiol (10 μM) was equivalent to 2-methoxyoestradiol (10 μM). A biophasic effect was observed with analogues including 2-methoxyoestrone and 2-methoxyoestriol, which enhanced thrombin-stimulated DNA synthesis at concentrations up to 3 μM, but the level of enhancement declined at 10 μM and is shown in FIG. 7. The effects of 17-β-oestradiol and 2-hydroxyoestradiol on protein synthesis are shown in Table 5.

TABLE 5

Effect of 2-methoxyoestradiol on protein synthesis rates in unstimulated smooth muscle cells.

| | [$^3$H]-leucine incorporation (% control) | | | | | |
|---|---|---|---|---|---|---|
| | 17β-oestradiol | | | 2-hydroxyoestradiol | | |
| Concentration | mean | ± | SEM | mean | ± | SEM |
| — | 100 | | | 100 | | |
| 0.3 | 103 | ± | 6 | 107 | ± | 3 |
| 1.0 | 89 | ± | 4 | 94 | ± | 10 |
| 3.0 | 87 | ± | 6 | 56 | ± | 8* |
| 10.0 | 100 | ± | 9 | 51 | ± | 10* |

*p < 0.05 paired Student's t-test, compared to 100% (no pretreatment)

We have shown here that 2-methoxyoestradiol, a natural metabolite of 17β-oestradiol which was previously thought to be inactive, has anti-inflammatory activities and inhibits the DNA synthesis and subsequent division of airway smooth muscle cells cultured from human bronchi.

The anti-inflammatory property renders the compound and its analogues useful in the treatment of inflammatory diseases, e.g. treatment of asthma and other chronic obstructive airway diseases, particularly those with demonstratable PMN involvement.

The inhibitory effect on DNA synthesis is not a result of cytotoxicity, since protein synthesis rates were not altered by incubation of cells with the highest concentrations of 2-methoxyoestradiol (10 μM) and no cell detachment from the culture plates was observed at this concentration. Without wishing to be bound by any proposed mechanism for the observed advantages, it is possible that the steroid inhibits the cells early in the G1 phase of the cell-cycle (2.0 hours post-mitogen), causing maximal inhibition of DNA synthesis. It remains .to be established whether post-mitogen addition of 2-methoxyoestradiol retains its anti-proliferative effect. 2-methoxyoestradiol inhibited responses to bFGF, thrombin and FCS (1%) with similar potencies, indicating that the effect was not specific to any one mitogen. This observation suggests that 2-methoxyoestradiol acts at early intracellular signalling step(s) used by each of these mitogens. Nevertheless, the inhibitory effect on DNA synthesis was surmountable, with higher concentrations of FCS (10%) being significantly less inhibited by preincubation with 2-methoxyoestradiol. This resistance could be explained by the greater response to the higher concentration of FCS, but a similar argument cannot be made for the resistance to inhibition when the mitogen is EGF, which elicited smaller responses than those elicited by thrombin, FCS 1% or bFGF. However, the proliferative effects of EGF and 10% FCS may be inhibited by 2-methoxyoestradiol. We do not yet have any evidence linking the inhibition of DNA synthesis to inhibition of cell proliferation. However, the fact that the latter effect is observed at lower concentrations of 2-methoxyoestradiol suggests that actions other than inhibition of DNA synthesis by 2-methoxyoestradiol also contribute to its anti-proliferative actions.

Several analogues of 2-methoxyoestradiol were examined to determine whether they shared this anti-proliferative effect. Both the parent compound 17β-oestradiol and the immediate precursor, 2-hydroxy-oestradiol, at lower concentrations increased DNA synthesis in response to FCS (1%) and inhibited DNA synthesis at 3 and 10 μM. It was not established whether these changes in DNA synthesis resulted in corresponding changes in cell proliferation. The enhancement of thrombin-stimulated DNA synthesis by 2-methoxyoestrone and 2-methoxyoestriol showed a bell-shaped concentration-response curve, with a lesser effect at the higher concentrations. Collectively, our observations suggest that 2-methoxyoestradiol is the most potent of the analogues examined, consistent with earlier observations on the proliferative responses of endothelial cells [Fotsis et al., 1994].

It may also be possible to administer the parent compound, 17β-estradiol, together with agents which induce metabolism to the active compound. For example, inducers of p450 cytochrome and of catecholamine methyl transferase may be used. Inhibitors of aryl sulphatase may also be considered.

The anti-proliferative effect of 2-methoxyoestradiol and its ability to reduce 5HT-induced increases in protein synthesis indicate both anti-hyperplastic and anti-hypertrophic effects. There is compelling evidence for hyperplasia and hypertrophy in asthmatic airways [Ebina et al., 1993], which account for a large part of the phenomenon of AHR [James et al., 1989]. Reductions in AHR are associated with complete resolution of symptoms in some asthmatics [Platts-Mills et al., 1987]. Moreover, of all the structural changes documented in the airway wall remodeling response in asthma, an increase in the airway smooth muscle is considered to be of greatest importance [Pare & Bai, 1995]. Thus a compound such as 2-methoxyoestradiol, which prevents the growth response of airway smooth muscle, would reduce AHR and therefore reduce the symptoms of asthma. In addition, the anti-angiogenic activity of 2-methoxyoestradiol [Fotsis et al., 1994] is likely to limit the remodelling response, since it has been established that there is an angiogenic component to the remodelling [Kuwano et al., 1993]. It seems likely that this angiogenesis is required to support the metabolic needs of the increased tissue mass. Therefore, prevention of the angiogenesis may arrest the remodelling response independently of any direct inhibitory effects of 2-methoxyoestradiol on smooth muscle and other cell types.

A number of other properties of 2-methoxyoestradiol are likely to be of therapeutic benefit in the treatment of asthma, including its established ability to disrupt microtubule formation [D'Amato et al., 1994], which may reduce the exocytotic release of inflammatory mediators from mast cells, macrophages and eosinophils.

Our data indicate that 2-methoxyoestradiol inhibits antigen-induced mast cell degranulation. This activity supports the use of 2-methoxyoestradiol in a wide range of allergic conditions, including allergic rhinitis and atopic skin conditions. Inhibition of guinea-pig peritoneal macrophage activation of fMLP suggests that the action of 2-methoxyoestradiol may extend beyond events associated with the cytoskeleton, since fMLF activates G-protein-linked receptors rather than phagocytosis.

In addition, the anti-oxidant activities of 2-methoxyoestradiol may also be of benefit, since the three key inflammatory cell types involved in airway inflammation each have the capacity to generate large amounts of oxygen radicals, and together with nitric oxide may cause significant oxidant damage. These activities also support the use of 2-methoxyoestradiol in the treatment of chronic obstructive airways disease, in which an important role for oxy radicals is well established and there is evidence of airway wall remodelling [Kuwano et al., 1993]. Finally, several studies indicate that 2-methoxyoestradiol and related compounds decrease calcium influx into smooth muscle [Goyache et al., 1995] which would, if also demonstrated for airways smooth muscle, counteract bronchospasm in asthma.

Although the examples have been described in some detail for the purpose of clarity and understanding, they represent guidelines only. The person skilled in the art will recognise that various modifications and alterations to the embodiments described herein may be made without departing from the scope of the invention.

References cited herein are listed on the following pages.

References

Aizu-Yokotta, E., Susaki, A. & Sato, Y. (1995). Natural estrogens induce modulation of microtubules in chinese hamster V79 cells in culture. *Cancer Research*, 55, 1863.

Brewster, C. E. P, Howarth, P. H., Djukanovic, R., Wilson, J., Holgate, S. T. & Roches, W. R. (1990). Myofibroblasts and subepithelial fibrosis in bronchial asthma. *Am. J. respir. Cell Mol. Biol.* 3, 507.

Goyache, F. M., Gutierrez, M., Hidalgo, A. & Cantabrana, B. (1995). Non-genomic effects of catecholestrogens in the in vivo rat uterine contraction. *General Pharmacology,* 26, 219.

D'Amato, R. J., Lin, C. M., Flynn, E., Folkman, J. & Hamel, E. (1994). 2-Methoxyoestradiol, an endogenous mammalian metabolite, inhibits tubulin polymerization by interacting at the colchicine site. *Proceedings of the National Academy of Sciences* (USA). 91,3964.

Dunhill, M. S., Massarella, G. R., Anderson, J. A. (1969). A comparison of the quantitative anatomy of the bronchi in normal subjects, in status asthmaticus, in chronic bronchitis, and in emphysema. *Thorax.* 24, 176.

Ebina, M., Takahashi, T., Chiba, T., Motomiya, M. (1993). Cellular hypertrophy and hyperplasia of airway smooth muscle underlying bronchial asthma. A 3-D morphometric study. *Am. Rev. Resp. Dis.* 148,720.

Fostis, T., Zhang, Y., Pepper, M. S., Adlecrutz. H., Montesano, R., Nawroth, P. & Schweiger, L. (1994). The endogenous oestrogen metabolite 2-methoxyoestradiol inhibits angiogenesis and suppresses tumour growth. *Nature*, 368,237.

Frigas, E., Motojima, S. & Gleich, G. J. (1991). The eosinophilic injury to the mucosa of the airways in the pathogenesis of bronchial asthma. *Eur J Respir Dis.*, 13, 123S.

Hirst, S. J., Barnes, P. J., Twort, C. H. C. (1992). Quantifying proliferation of cultured human and rabbit airway smooth muscle cells in response to serum and platelet-derived growth factor. *Am. J. Resp. Cell. Mol. Biol.* 7, 574.

James, A. L., Pare, P. D., Hogg, J. C. (1989). The mechanics of airway narrowing in asthma. *Am. Rev. Respir. Dis.*, 139,242, Klauber, N., Panangi, S., Flynn, E., Hanel, E. & D'Amato, R. J. (1997) Inhibition of angiogenesis and breast cancer in mice by the microtubule inhibitors 2-methoxyoestradiol and taxol. Cancer Research 57: 81–86.

Kuwano, K., Bosken, C. H., Pase, P. D., Bai, T. R., Wiggs, B. R. & Hogg, J. C. (1993). Small airways dimensions in asthma and chronic airway obstructive pulmonary disease *Am. Rev. Resp. Dis.*, 148,1220.

Lottering, M. L., Haag, M. & Seegers, J. C. (1992). Effects of 17-β-oestradiol metabolites on cell cycle events in MCF-7 cells. *Cancer Research*, 52,5926.

Lungren, R., Soderberg, M., Horstedt, P. and Stenling, R. (1988). Morphological studies on bronchial mucosa biopsies from asthmatics before and after ten years of treatment with inhaled steroids. *Eur. Repir. J.*, 1,883.

Menegazzi, R., Zaborchi, G., Knowles, A., Cramer, C. and Patrarca, P. (1992). A new one-step assay on whole cell suspensions for peroxidase secretion by human neutrophils and oesinophils. J. Leuk-Biol. 52:612.

Merriam, G. R., Machusky, N. J., Picard, M. K. & Naftolin, F. (1980) Comparative properties of the catecholestrogens, I: methylation by catechol-O-methyltransferase and binding to cytosol estrogen receptors. Steroids, 36: 1–11.

Nishigaki, I., Sasguri, Y. & Yagi, K. (1995). Anti-proliferative effect of 2-methoxyoestradiol on cultured smooth muscle cells from rabbit aorta. *Atherosclerosis*, 113,167.

Pare, P. & Bai, T. R. (1995). The consequences of chronic allergic inflammation. *Thorax*, 50,328.

Platts-Mills, T. A. E. & Chapman, M. D. (1987). Dust mites: immunology, allergic disease, and environmental control. *J. Allergy Clin. Immunol.*, 80, 755.

Rosner, W., Hryb, D. J., Khan, M. S., Nakhla, A. M. & Ronmas, N. A. (1991). Sex-hormone binding globulin: anatomy and physiology of a new regulatory system. *Journal of Steroid Biochemistry & Molecular Biology*, 40,813.

Shelton, M. J and Hosking S. (1975) Neutrophil and Opsonic function in children with recurrent infections I. Neurophil iodination. Aust. J. Med. Tech. 6:54.

Sotomayor, H., Badier, M. M Vervloet, D., Orehek, J. (1984). Seasonal increase of carbachol airway responsiveness in patients allergic to grass pollen. Reversal by corticosteroids. *Am. Rev. Resp. Dis.*, 130,56.

Spink, D. C., Hayes, C. L., Young, N. R., Christou, M., Sutter, T. R., Jefcoate, C. R. & Gierthy, J. F. (1994). The effect of 2,3,7,8-tetrachlorodibenzo-p-dioxin on estrogen metabolism in MCF-7 breast cancer cells: evidence for induction of a novel 17-beta estradiol 4-hydroxylase. *Journal of Steroid Biochemistry & Molecular Biology*, 51,251.

Stewart A G, and Harris T. (1992). Adenosine inhibits platelet-activating factor but not tumour necrosis factor α-induced priming of human neutrophils. Immunology 78:152–158.

Stewart A G, Tomlinson P R T & Wilson J W. (1995a). Regulation of airway wall remodelling: prospects for the development of novel anti-asthma drugs. *Advances in Pharmacology* 33,200.

Stewart A G, Fernandes D J, & Tomlinson P R T. (1995b). Glucocorticoids inhibit mitogenic responses of human cultured airway smooth muscle. *British Journal of Pharmacology* 116,3219.

Stewart, A. G. & Phillips, W. A. (1989) Intracellular platelet-activating factor regulates eicosanoid generation in guinea-pig peritoneal macrophages. British Journal of Pharmacology, 98: 141–148.

Stewart A G, Tomlinson P R, Fernandes D J, Wilson J and Harris T (1995c). Tumour necrosis factor α modulates mitogenic responses of human cultured airway smooth muscle. *AM. J. Respir. Cell Mol. Biol.* 12,110.

Stewart A G, Tomlinson P R T, & Wilson, J. (1993). Airway wall remodelling in asthma: a novel target for the development of anti-asthma drugs. *Trends in Pharmacological Sciences* 14.275.

Stewart A G, Schachte L & Tomlinson P R. (1997). Regulation of airway smooth muscle proliferation by $\beta_2$-adrenoceptor agonists. In: (Ed. A G Stewart) Airway wall remodelling in the pathogenesis of asthma. CRC PRess. Boca Raton, chapter 11 pages 295–335.

Tomlinson P R T, Wilson J & Stewart A G. (1994). Inhibition by salbutamol of the proliferation of human airway smooth muscle cells grown in culture. *British Journal of Pharmacology* 111,641.

Tomlinson P R T, Wilson J W & Stewart A G. (1995). Salbutamol inhibits the proliferation of human airway smooth muscle cells grown in culture: relationship to elevated cAMP levels. *Biochemical Pharmacology* 49,1809.

Wahedna, I Wong, C. S. Wisniewski, A. F. Z., Pavord, I. D. & Tattersfield, A. E. (1993). Asthma control during and after cessation of regular β2-agonist treatment. *Am Rev Respir. Dis.*, 148,707.

Zhang, Z & Davis, D. L. (1992). Cell-type specific responses in prostaglandin secretion by glandular and stromal cells from pig endometrium treated with catecholestrogens, methoxyestrogens and progesterone. *Prostaglandins*, 44,53–64.

I claim:

1. A method of treating a disease characterized by chronic or acute airway inflammation, comprising the step of administering an effective amount of a steroid or steroid analogue selected from the group consisting of 2-methoxyoestradiol, 2-hydroxyoestradiol, 2-methoxyestrone, 2-methoxyoestradiol-3-methyl ether, and 4 methoxyoestradiol.

2. A method according to claim 1, wherein the steroid is 2-methoxyoestradiol.

3. A method according to claim 2, wherein the disease to be treated is selected from the group consisting of asthma, airway hyperresponsiveness, brochoconstriction, emphysema, pheumonia, atopic disease and pulmonary infection.

4. A method according to claim 1, wherein the disease is asthma.

5. A method according to claim 1, wherein the steroid or steroid analogue is administered in combination with a pharmaceutically acceptable carrier.

6. A method according to claim 1, wherein the steroid or steroid analogue is administered by a route selected from the group consisting of topical, oral and nasal administration.

7. A method according to claim 6, wherein the steroid or steroid analogue is administered by nasal administration.

8. A method according to claim 7, wherein the steroid or steroid analogue is administered by inhalation.

9. A method according to claim 1, wherein the steroid or steroid analogue is administered in a form selected from the group consisting of capsules, cachets, tablets, aerosols, powder granules, micronised particles and solutions.

* * * * *